(12) United States Patent
Ball et al.

(10) Patent No.: US 8,788,444 B2
(45) Date of Patent: Jul. 22, 2014

(54) DATA ANALYSIS METHOD AND SYSTEM

(75) Inventors: Graham Ball, Nottingham (GB); Lee Lancashire, Greater Manchester (GB)

(73) Assignee: Nottingham Trent University, Nottingham (GB)

( * ) Notice: Subject to any disclaimer, the term of this patent is extended or adjusted under 35 U.S.C. 154(b) by 559 days.

(21) Appl. No.: 13/125,054

(22) PCT Filed: Oct. 20, 2009

(86) PCT No.: PCT/GB2009/051412
§ 371 (c)(1),
(2), (4) Date: Aug. 4, 2011

(87) PCT Pub. No.: WO2010/046697
PCT Pub. Date: Apr. 29, 2010

(65) Prior Publication Data
US 2011/0282819 A1   Nov. 17, 2011

(30) Foreign Application Priority Data

Oct. 20, 2008 (GB) .................................. 0819221.3

(51) Int. Cl.
*G06N 5/00* (2006.01)
(52) U.S. Cl.
USPC .............................. 706/25; 700/250; 702/19
(58) Field of Classification Search
None
See application file for complete search history.

(56) References Cited

U.S. PATENT DOCUMENTS

| 2004/0199482 | A1 | 10/2004 | Wilson | |
|---|---|---|---|---|
| 2008/0319933 | A1* | 12/2008 | Moussa et al. | 706/31 |
| 2009/0075360 | A1* | 3/2009 | Ho et al. | 435/284.1 |
| 2010/0100248 | A1* | 4/2010 | Minto et al. | 700/287 |

FOREIGN PATENT DOCUMENTS

| WO | 99/09507 | 2/1999 |
|---|---|---|
| WO | 02/06829 | 1/2002 |
| WO | 03/079286 | 9/2003 |

OTHER PUBLICATIONS

Floyd et al., Cancer, 74:2944-2948 (1994). "Prediction of breast cancer malignancy using an artificial neural network."
Lancashire et al., Current Proteomics, 2:15-29 (2005). "Current developments in the analysis of proteomic data: Artificial neural network data mining techniques for the identification of proteomic biomarkers related to breast cancer."

* cited by examiner

*Primary Examiner* — Alan Chen
*Assistant Examiner* — Kalpana Bharadwaj
(74) *Attorney, Agent, or Firm* — Nixon Peabody LLP

(57) ABSTRACT

The present invention relates to the analysis of data to identify relationships between the input data and one or more conditions. One method of analyzing such data is by the use of neural networks which are non-linear statistical data modelling tools, the structure of which may be changed based on information that is passed through the network during a training phase. A known problem that affects neural networks is the issue of overtraining which arises in overcomplex or overspecified systems when the capacity of the network significantly exceeds the needed parameters. The present invention provides a method of analyzing data using a neural network with a constrained architecture that mitigates the problems associated with the prior art.

16 Claims, 30 Drawing Sheets

FIGURE 3

| SAMPLE | GENE | EXPRESSION DATA | CANCER/HEALTHY |
|---|---|---|---|
| 1 | A<br>B<br>C<br>D<br>E<br>F<br>G<br>H<br>I<br>J | $A_1$<br>$B_1$<br>$C_1$<br>$D_1$<br>$E_1$<br>$F_1$<br>$G_1$<br>$H_1$<br>$I_1$<br>$J_1$ | C |
| 2 | A<br>B<br>C<br>D<br>E<br>F<br>G<br>H<br>I<br>J | $A_2$<br>$B_2$<br>$C_2$<br>$D_2$<br>$E_2$<br>$F_2$<br>$G_2$<br>$H_2$<br>$I_2$<br>$J_2$ | H |
| ⋮ | | | |
| 10 | A<br>B<br>C<br>D<br>E<br>F<br>G<br>H<br>I<br>J | $A_{10}$<br>$B_{10}$<br>$C_{10}$<br>$D_{10}$<br>$E_{10}$<br>$F_{10}$<br>$G_{10}$<br>$H_{10}$<br>$I_{10}$<br>$J_{10}$ | C |

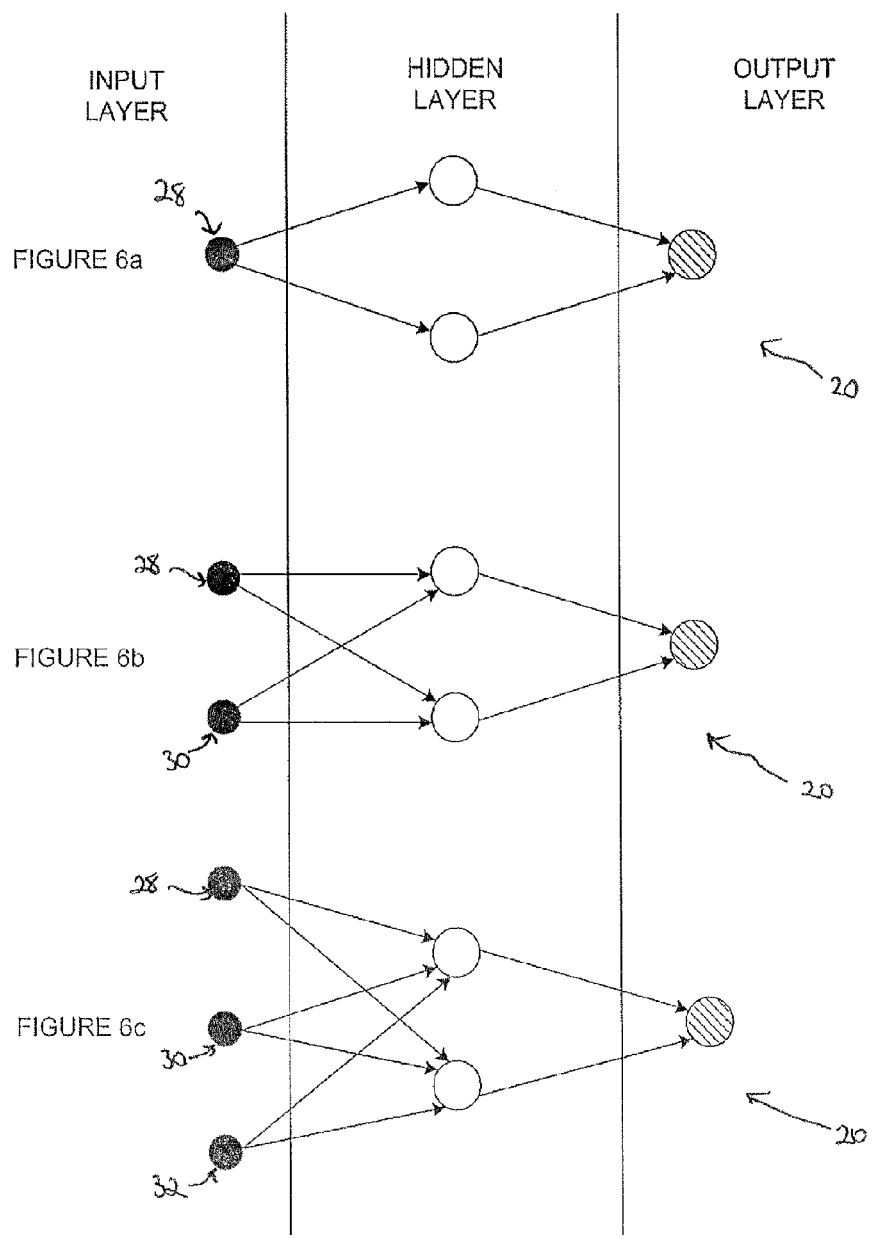

Comparison of performance of random model to those generated with stepwise approach.

DATA ANALYSIS METHOD AND SYSTEM

CROSS REFERENCE TO RELATED APPLICATIONS

This application is a 371 National Phase Entry Application of International Application No. PCT/GB2009/051412 filed Oct. 20, 2009, which designates the U.S., and which claims the benefit of priority of Great Britain Application No. 0819221.3 filed Oct. 20, 2008, the contents of which are incorporated herein by reference in their entirety.

FIELD OF INVENTION

The present invention relates to a method of analysing data and in particular relates to the use of artificial neural networks (ANNs) to analyse data and identify relationships between input data and one or more conditions.

BACKGROUND TO THE INVENTION

An artificial neural network (ANN), or "neural network", is a mathematical or computational model comprising an interconnected group of artificial neurons which is capable of processing information so as to model relationships between inputs and outputs or to find patterns in data.

A neural network may therefore be considered as a non-linear statistical data modelling tool and generally is an adaptive system that is capable of changing its structure based on external or internal information that flows through the network in a training phase. The strength, or weights, of the connections in the network may be altered during training in order to produce a desired signal flow.

Various types of neural network can be constructed. For example, a feedforward neural network is one of the simplest types of ANN in which information moves only in one direction and recurrent networks are models with bi-directional data flow. Many other neural network types are available.

One particular variation of a feedforward network is the multilayer perceptron which uses three or more layers of neurons (nodes) with nonlinear activation functions, and is more powerful than a single layer perceptron model in that it can distinguish data that is not linearly separable.

The ability of neural networks to be trained in a learning phase enables the weighting function between the various nodes/neurons of the network to be altered such that the network can be used to process or classify input data. Various different learning models may be used to train a neural network such as "supervised learning" in which a set of example data that relates to one or more outcomes or conditions is used to train the network such that it can, for example, predict an outcome for any given input data. Supervised learning may therefore be considered as the inference of a mapping relationship between input data and one or more outcomes.

Training an artificial neural network may involve the comparison of the network output to a desired output and using the error between the two outputs to adjust the weighting between nodes of the network. In one learning model a cost function C may be defined and the training may comprise altering the node weightings until the function C can no longer be minimised further. In this way a relationship between the input data and an outcome or series of outcomes may be derived. An example of a cost function might be $C=E[(f(x)-y)^2]$ where $(x, y)$ is a data pair taken from some distribution D.

In one application, a neural network might be trained with gene expression data from tissues taken from patients who are healthy and from patients who have cancer. The training of the network in such an example may identify genes or gene sets that are biomarkers for cancer. The trained network may be used to predict the likelihood of a given person developing cancer based on the results of an analysis of a tissue sample.

Another field of technology in which an artificial neural network might be used is meteorology in which, for example, temperature or pressure data at a series of locations over time could be used to determine the likelihood of there being rainfall at a given location at a given time.

A known problem with artificial neural networks is the issue of overtraining which arises in overcomplex or over-specified systems when the capacity of the network significantly exceeds the needed free parameters. This problem can lead to a neural network suggesting that particular parameters are important whereas in reality they are not. This is caused by the identification of a set of parameters having a higher importance and by the false detection of parameters. These parameters are likely to have a lower performance when classifying unseen data/cases.

It is an object of the present invention to provide a method of analysing data using a neural network that overcomes or substantially mitigates the above mentioned problem.

STATEMENTS OF INVENTION

According to a first aspect the present invention provides a method of determining a relationship between input data and one or more conditions comprising the steps of: receiving input data categorised into one or more predetermined classes of condition; training an artificial neural network with the input data, the artificial neural network comprising an input layer having one or more input nodes arranged to receive input data; a hidden layer comprising two or more hidden nodes, the nodes of the hidden layer being connected to the one or more nodes of the input layer by connections of adjustable weight; and, an output layer having an output node arranged to output data related to the one or more conditions, the output node being connected to the nodes of the hidden layer by connections of adjustable weight; determining relationships between the input data and the one or more conditions wherein the artificial neural network has a constrained architecture in which (i) the number of hidden nodes within the hidden layer is constrained; and, (ii) the initial weights of the connections between nodes are restricted.

The present invention provides a method of analysis that that highlights those parameters in the input data that are particularly useful for predicting whether a given outcome is likely. In other words, compared to prior art systems the method of the present invention effectively increases the difference or "contrast" between the various input parameters so that the most relevant parameters from a predictive capability point of view are identified.

The present invention provides a method of determining a relationship between input data and one or more conditions using an artificial neural network. The ANN used in the invention has a constrained architecture in which the number of nodes within the hidden layer of the ANN are constrained and in which the initial weights of the connections between nodes are restricted.

The method of the present invention therefore proposes an ANN architecture which runs contrary to the general teaching of the prior art. In prior art systems the size of the hidden layer is maximised within the constraints of the processing system being used whereas in the present invention the architecture is deliberately constrained in order to increase the effectiveness of the predictive capability of the network and the contrast between markers of relevance and non relevance within a highly dimensional system. In comparison to known systems, the present invention provides the advantage that the predictive performance for the markers that are identified is improved and those markers identified by the method according to the present invention are relevant to the underlying process within the system.

Preferably in order to maximise the predictive effectiveness of the present invention the number of hidden nodes is in the range two to five. More preferably the number of hidden nodes is set at two.

Preferably the initial weights of the connections between nodes have a standard deviation in the range 0.01 to 0.5. It is noted that lowering the standard deviation makes the artificial neural network less predictive. Raising the standard deviation reduces the constraints on the network. More preferably, the initial weights of connections between nodes have a standard deviation of 0.1.

Conveniently the input data comprises data pairs (e.g. gene and gene expression data) which are categorised into one or more conditions (e.g. cancerous or healthy). In the example of gene data then the gene may be regarded as a parameter and the expression data as the associated parameter value. Furthermore, input data may be grouped into a plurality of samples, each sample having an identical selection of data pairs (e.g. the gene and gene expression data may detail the condition—healthy/cancerous—of a plurality of individuals).

Training of the neural network may conveniently comprise selecting a particular parameter in each sample (i.e. the same parameter in each sample) and then training the network with the parameter value associated with the selected parameter. The performance of the network may be recorded for the selected parameter and then the process may be repeated for each parameter in the samples in turn.

The determining step of the first aspect of the invention may comprise ranking the recorded performance of each selected parameter against the known condition and the best performing parameter may then be selected.

Once the best performing parameter from the plurality of samples has been determined then a further selecting step may comprise pairing that best performing parameter with one of the remaining parameters. The network may then be further trained with the parameter values associated with the pair of selected parameters and the network performance recorded. As before, the best performing parameter may then be paired with each of the remaining parameters in turn.

The selecting, training and recording steps may then be repeated, adding one parameter in turn to the known best performing parameters until no further substantial performance increase is gained.

Conveniently it is noted that the input data may be grouped into a plurality of samples, each sample having an identical selection of data pairs, each data pair being categorised into the one or more conditions and comprising a parameter and associated parameter value, and the training and determining steps of the first aspect of the invention may comprise: selecting a parameter within the input data, training the artificial neural network with corresponding parameter values and recording artificial neural network performance; repeating for each parameter within the input data; determining the best performing parameter in the input data; and, repeating the selecting, repeating and determining, each repetition adding one of the remaining parameters to the best performing combination of parameters, until artificial neural network performance is not improved.

In one application of the method according to an embodiment of the present invention the parameters may represent genes and the parameter values may represent gene expression data. In a further application the parameter may represent proteins and the parameter values may represent activity function.

In other applications of the method according to an embodiment of the present invention the parameter may represent a meteorological parameter, e.g. temperature or rainfall at a given location and the parameter value may represent the associated temperature or rainfall value.

It is however noted that the method according to the present invention may be applied to any complex system where there are a large number of interacting factors occurring in different states over time.

According to a second aspect of the present invention there is provided a method of determining a relationship between input data and one or more conditions comprising: receiving input data categorised into one or more predetermined classes of condition; determining relationships between the input data and the one or more conditions using a neural network, the artificial neural network comprising an input layer having one or more input nodes arranged to receive input data; a hidden layer comprising two or more hidden nodes, the nodes of the hidden layer being connected to the one or more nodes of the input layer by connections of adjustable weight; and, an output layer having an output node arranged to output data related to the one or more conditions, the output node being connected to the nodes of the hidden layer by connections of adjustable weight wherein the artificial neural network has a constrained architecture in which (i) the number of hidden nodes within the hidden layer is constrained; and, (ii) the initial weights of the connections between nodes are restricted.

According to a third aspect of the present invention there is provided an artificial neural network for determining a relationship between input data and one or more conditions comprising: an input layer having one or more input nodes arranged to receive input data categorised into one or more predetermined classes of condition; a hidden layer comprising two or more hidden nodes, the nodes of the hidden layer being connected to the one or more nodes of the input layer by connections of adjustable weight; and, an output layer having an output node arranged to output data related to the one or more conditions, the output node being connected to the nodes of the hidden layer by connections of adjustable weight; wherein the artificial neural network has a constrained architecture in which (i) the number of hidden nodes within the hidden layer is constrained; and, (ii) the initial weights of the connections between nodes are restricted.

The invention extends to a computer system for determining a relationship between input data and one or more conditions comprising an artificial neural network according to the third aspect of the present invention.

It will be appreciated that preferred and/or optional features of the first aspect of the invention may be provided in the second and third aspects of the invention also, either alone or in appropriate combinations.

BRIEF DESCRIPTION OF THE DRAWINGS

In order that the invention may be more readily understood, reference will now be made, by way of example, to the accompanying drawings in which:

FIG. 3 is a representation of gene expression data to be used in conjunction with an artificial neural network in accordance with an embodiment of the present invention;

FIG. 6 shows how the artificial network in accordance with the present invention develops as the input data set is used;

DETAILED DESCRIPTION OF THE INVENTION

One drawback of traditional linear based ANN models is that they often cannot generalise well to problems and therefore may only be applicable to the dataset they are originally applied to. Simulation experiments have shown that stepwise logistic regression has limited power in selecting important variables in small data sets, and therefore risks overfitting (Steyerberg, E. W., Eijkemans, M. J. and Habbema, J. D. (1999) Stepwise selection in small data sets: a simulation study of bias in logistic regression analysis, *J Clin Epidemiol*, 52, 935-942.). Additionally the automatic selection procedure is non-subjective and ignores logical constraints. The applied neural network stepwise approach of the present invention does not share the limitations of the prior art because the models have been shown to be applicable to a separate datasets used for validation, so are capable of generalisation to new data and as such, overfitting has not been observed when using this approach.

Figure 1:
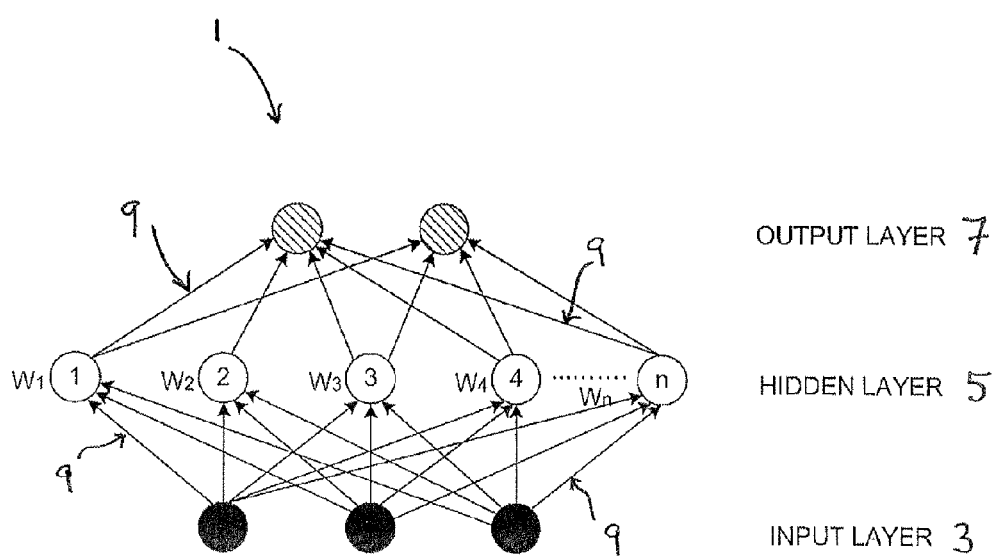
FIG. 1 shows a representation of a typical (known) artificial neural network.

FIG. 1 is a dependency tree style representation of an artificial neural network 1. It can be seen that the network 1 depicted in the Figure divides into three basic layers: an input layer 3 which receives input data; a hidden layer 5, and; an output layer 7 which returns a result. In the example of FIG. 1 there are three input level nodes, n hidden layer nodes (of which only five are shown for clarity) and two output layer nodes.

It is noted that the number of hidden layers may be varied.

The various interconnections between the nodes are indicated in FIG. 1 by the connecting arrows 9. For the first node in the input layer the various weights attributed to the connections to the hidden layer nodes are indicated by the weights $w_1$, $w_2$, $w_3$, $w_4$ and $w_n$. For clarity the weights on the remaining connections are not shown in this Figure.

The neural network is arranged such that input data is fed into the input layer 3 and is then multiplied by the interconnection weights as it is passed from the input layer 3 to the hidden layer 5. Within the hidden layer 5, the data is summed then processed by a nonlinear function (for example a hyperbolic tangent function or a sigmoidal transfer function). As the processed data leaves the hidden layer to the output later 7 it is, again multiplied by interconnection weights, then summed and processed within the output layer to produce the neural network output.

One of the most popular training algorithms for multi-layer perceptron and many other neural networks is an algorithm called backpropagation. With backpropagation, the input data is repeatedly presented to the neural network. With each presentation the output of the neural network is compared to the desired output and an error is computed. This error is then fed back (backpropagated) to the neural network and used to adjust the weights such that the error decreases with each iteration and the neural model gets closer and closer to producing the desired output. This process is known as "training".

Figure 2:
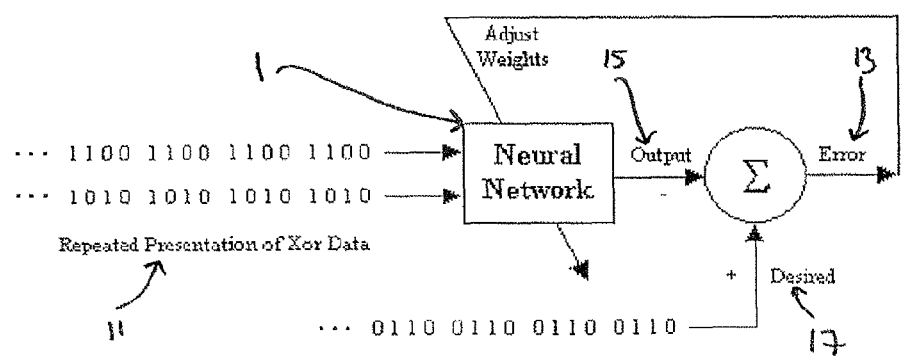
FIG. 2 illustrates the mechanism of neural network learning.

FIG. 2 is a representation of the training of a neural network 1. During training the network is repeatedly presented with input data 11 (in this case exclusive-or data, Xor data). Each time the data 11 is presented the error 13 between the network output 15 and the desired output 17 is computed and fed back to the neural network 1. The neural network 1 uses this error to adjust its weights such that the error will be decreased. This sequence of events is usually repeated until an acceptable error has been reached or until the network no longer appears to be learning.

When training a neural network the learning rate is a parameter found in many learning algorithms that alters the speed at which the network arrives at the minimum solution. If the rate is too high then the network can oscillate about the solution or diverge from the solution. If the rate is too low then the network may take too long to reach the solution.

A further parameter that may be varied during the training of an artificial neural network is the momentum parameter that is used to prevent the network from converging on a local minimum or saddle point. An overly high momentum parameter can risk overshooting the minimum. A momentum parameter that is too low can result in a network that cannot reliably avoid local minima.

Having discussed the use and training of artificial neural networks, the application of a neural network in the context of embodiments of the present invention is discussed below. It is noted that while the example discussed below relates to bioinformatics, the invention described herein is applicable to other fields of technology, e.g. meteorological predictions, pollution prediction, environmental prediction etc.

FIG. 3 is a highly generalised set of gene and gene expression data across 10 individuals (samples). For each sample, the same set of genes and their associated gene expression data are detailed along with a condition or state, in this case "healthy" or "cancer". The processing of this data set in the context of the present invention is described in relation to the flow chart of FIG. 5 and the network representations of FIGS. 4 and 6.

Figure 4:
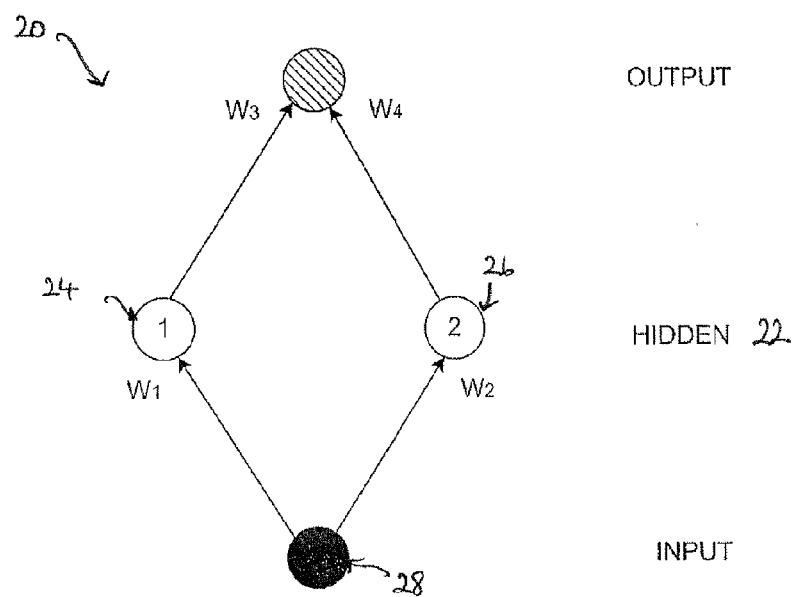
FIG. 4 shows an artificial neural network in accordance with an embodiment of the present invention.

FIG. 4 depicts the initial form of an artificial neural network 20 used in conjunction with the method of the present invention. As can be seen from the figure, the hidden layer 22 comprises only two nodes (24, 26) as opposed to the 20+ nodes found in prior art systems. Initially there is a single input node 28 but as described below in relation to FIGS. 5 and 6 the number of input nodes will gradually be increased until the performance of the neural network cannot be improved further.

As noted above a known problem with neural networks is the fact that they can be over-trained such that relationships can be derived between the input and output data for virtually all of the input data parameters.

In the artificial neural network in accordance with embodiments of the present invention the network is set up to as to improve the network's ability to identify the most relevant input parameters. To this end, the number of nodes within the hidden layer is restricted, preferably below five nodes and particularly to two nodes. In addition to this the standard deviation between the initial weights of the interconnections between nodes is also constrained. Preferably, the standard deviation, $\sigma$, of the initial weights of the interconnections are placed in the range 0.01 to 0.5 with an optimum value of 0.1.

Figure 5:
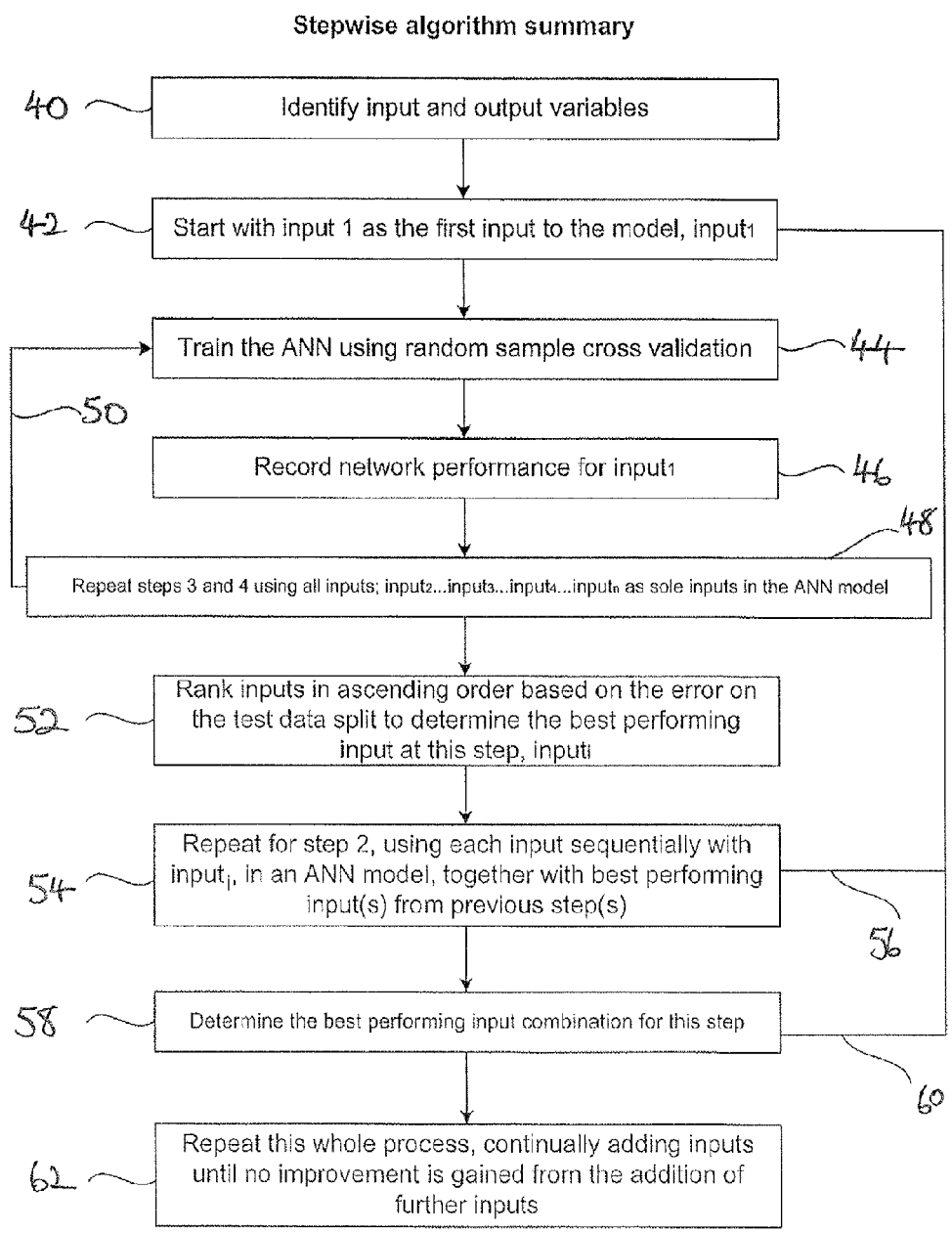
FIG. 5 is a flow chart detailing the operation of a system which incorporates an artificial neural network in accordance with an embodiment of the present invention.
Figure 7A:
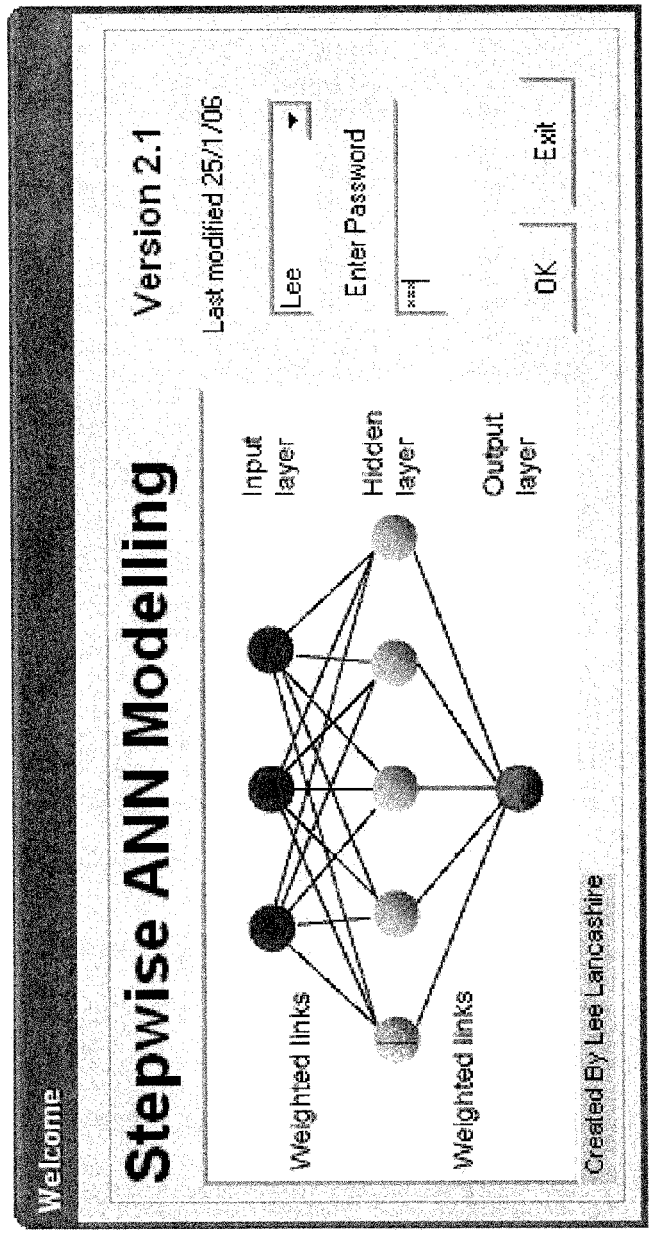
FIG. 7 (a)-(g) shows screenshot diagrams from the Stepwise ANN modeling software of the invention. Each diagram (a)-(g) represents a different option screen available within the software for model building and analysis.
Figure 7B:
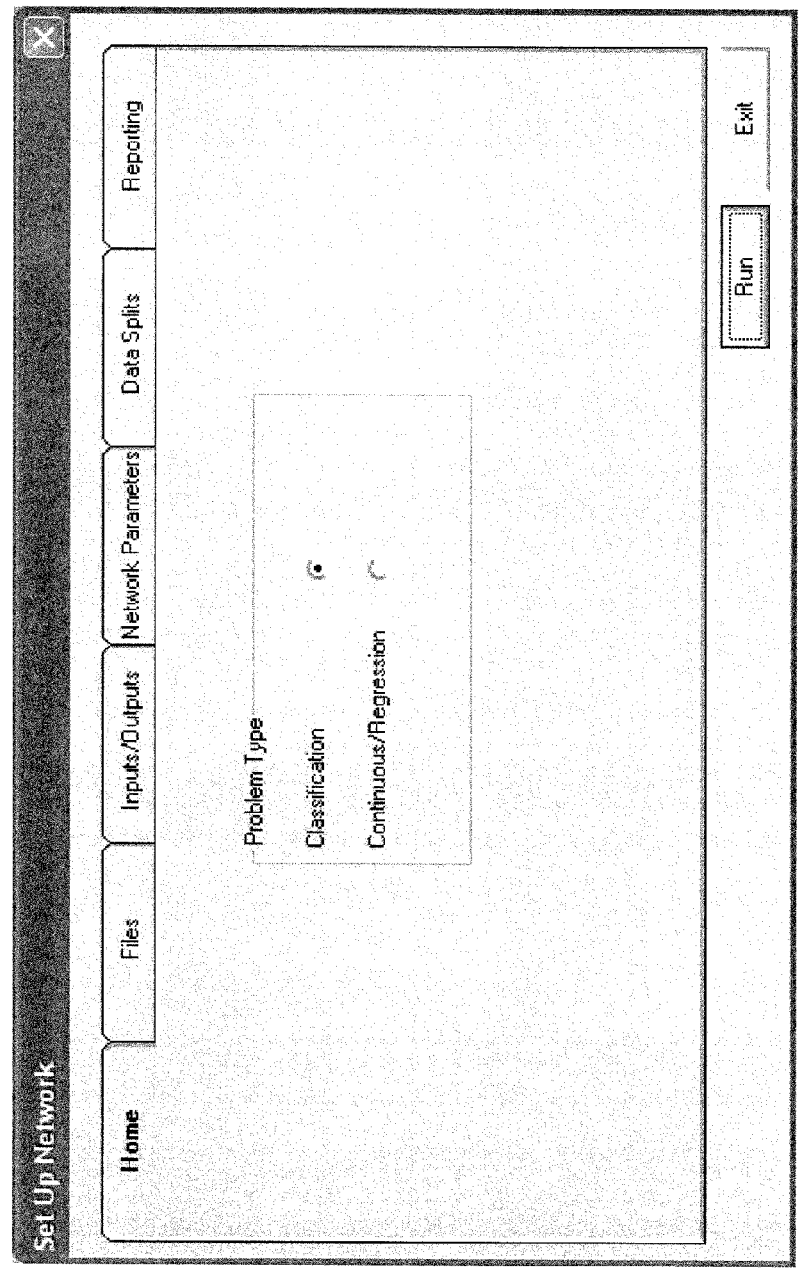
Figure 7C:
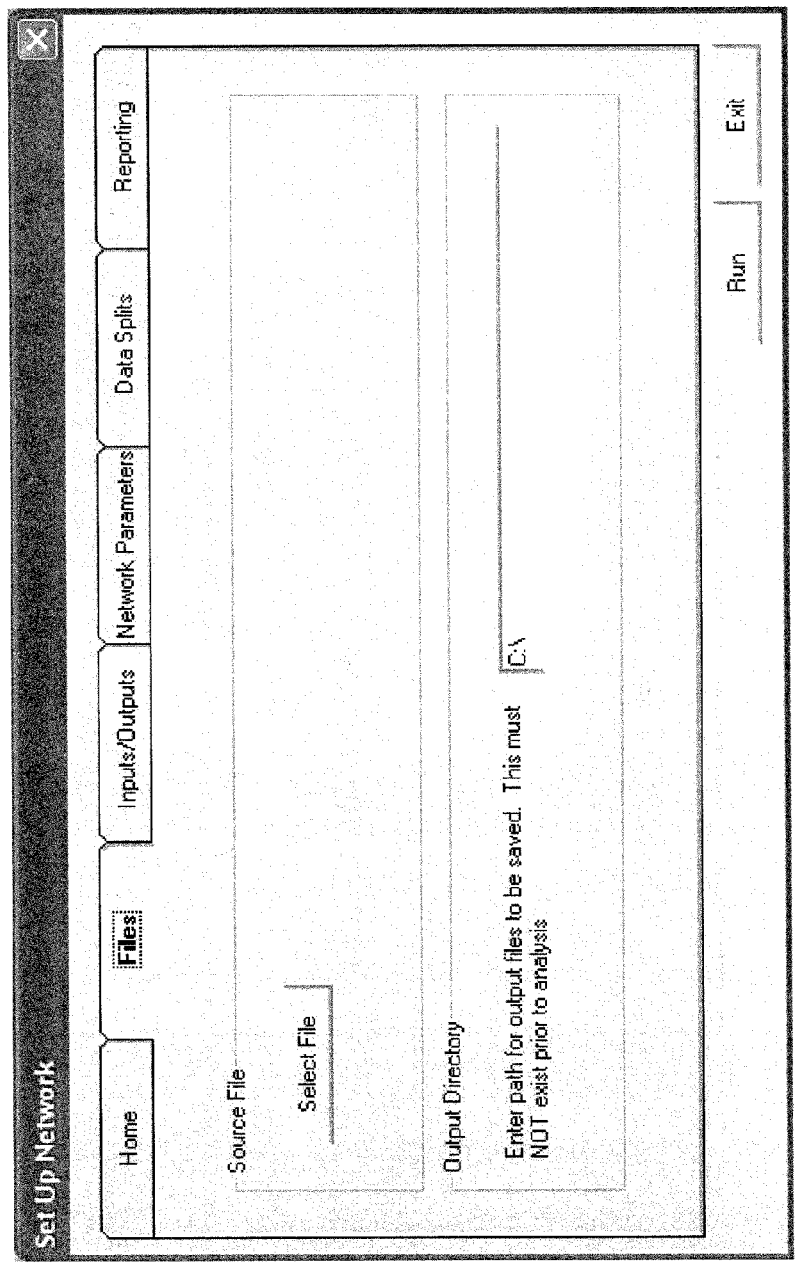
Figure 7D:
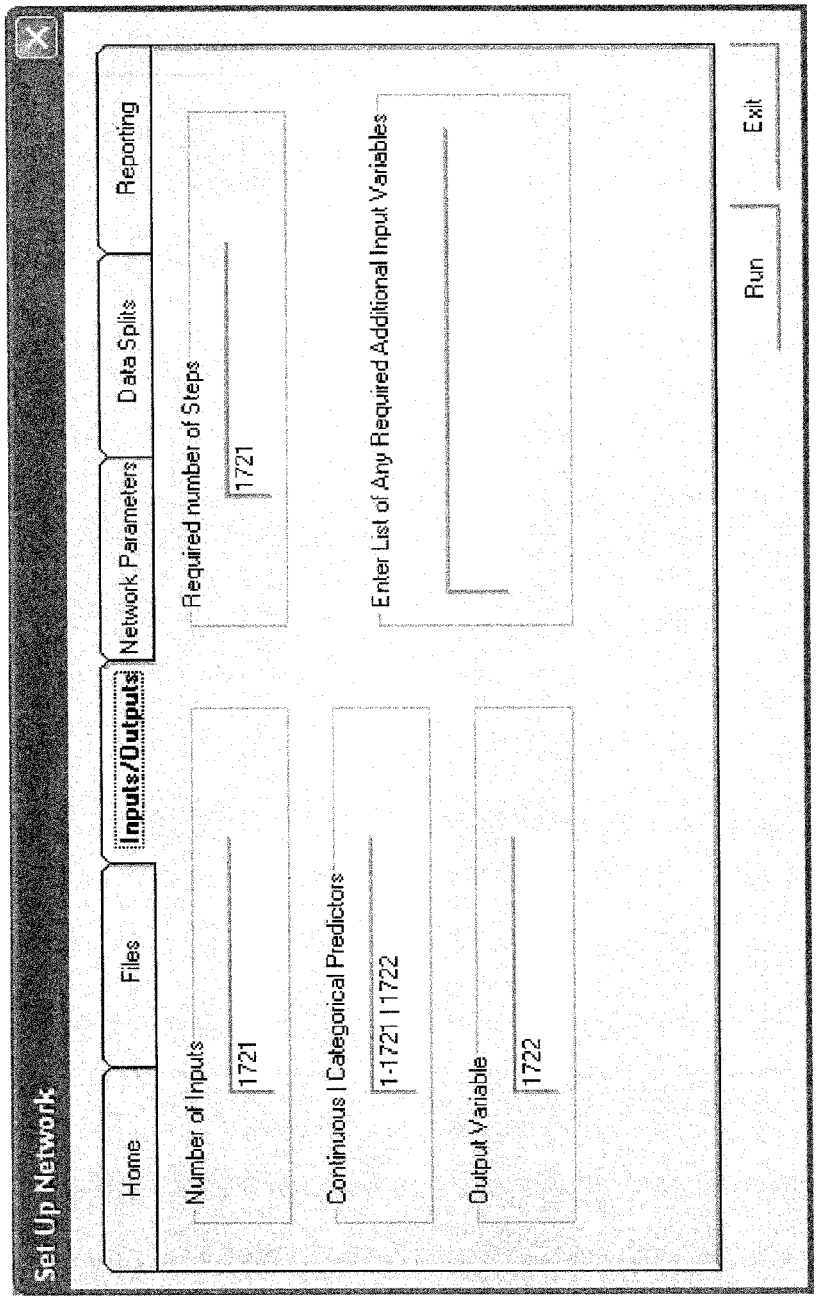
Figure 7E:
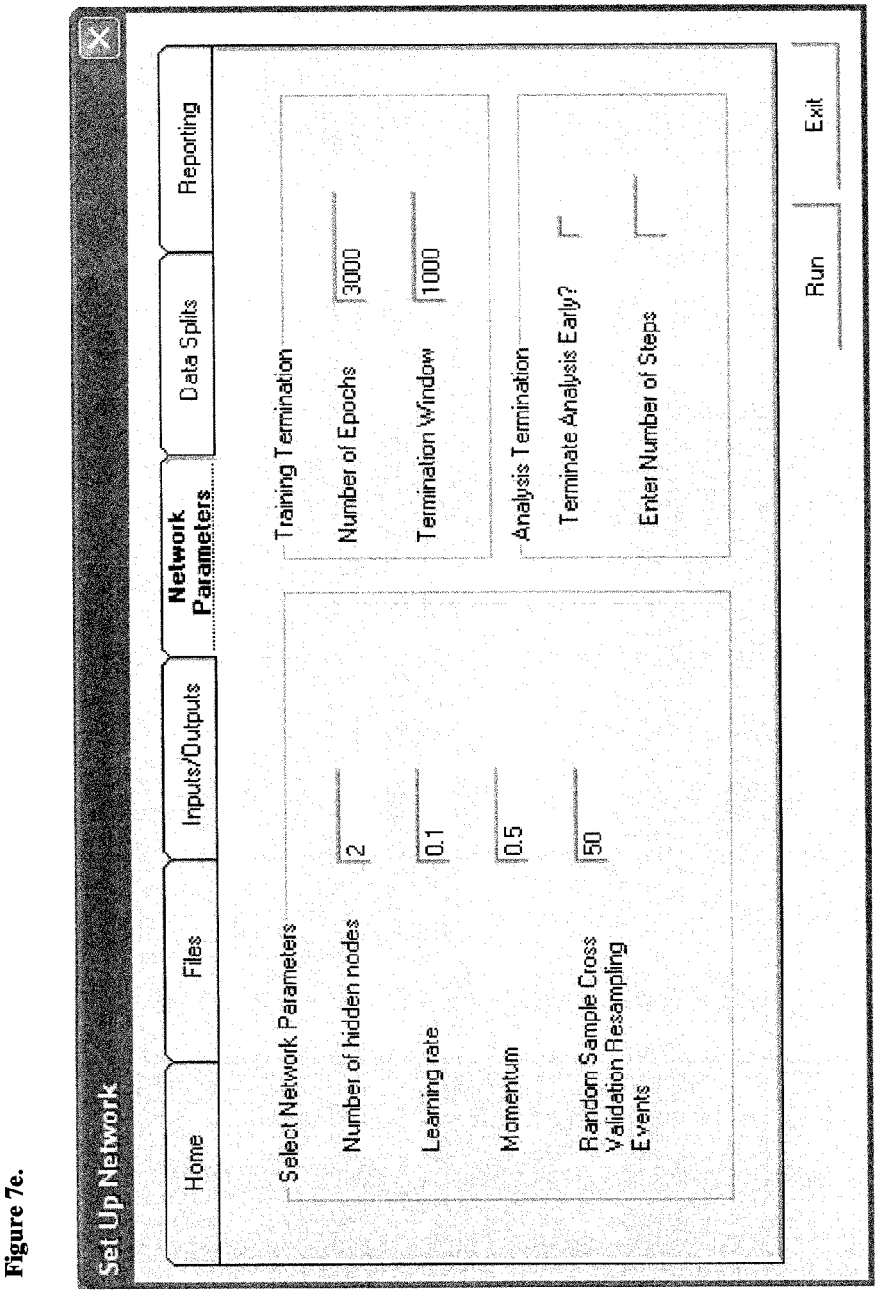
Figure 7F:
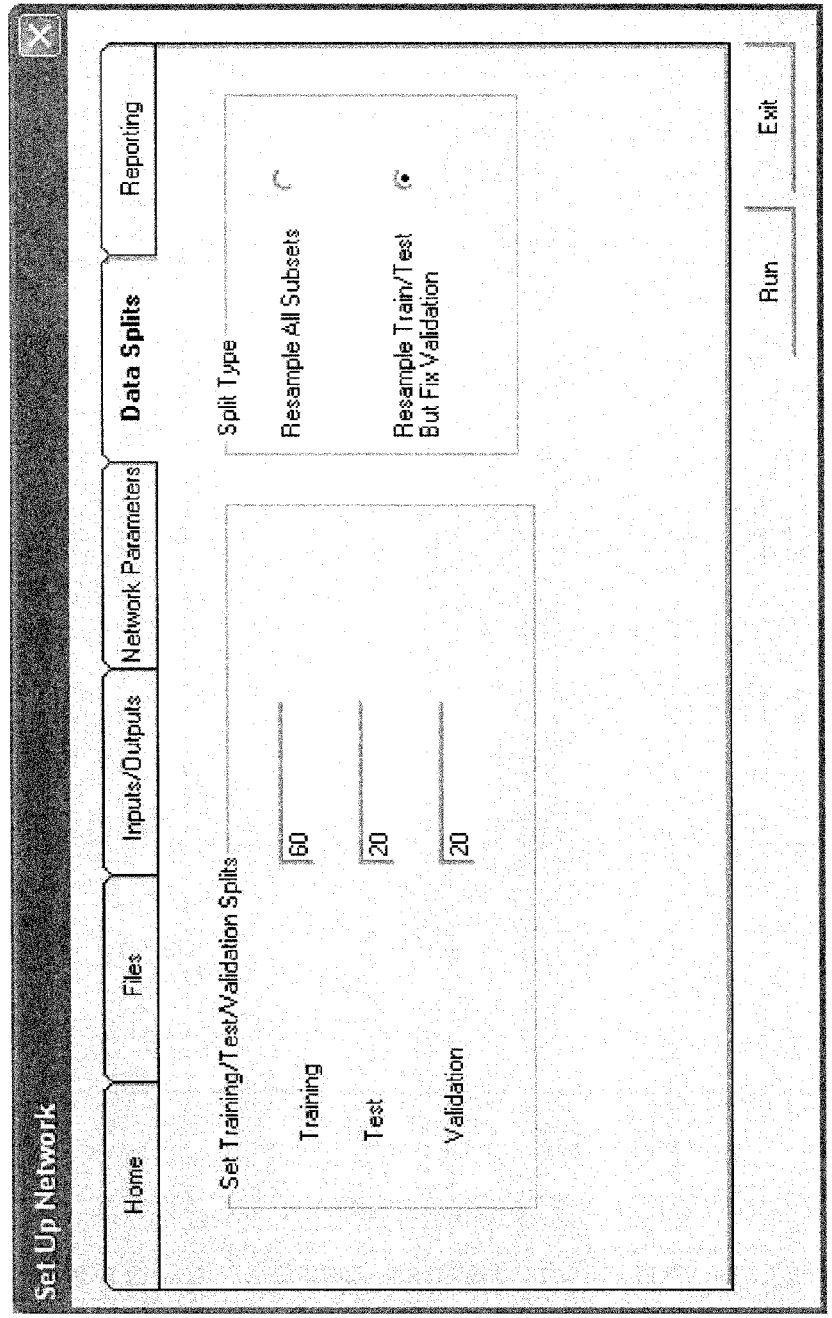
Figure 7G:
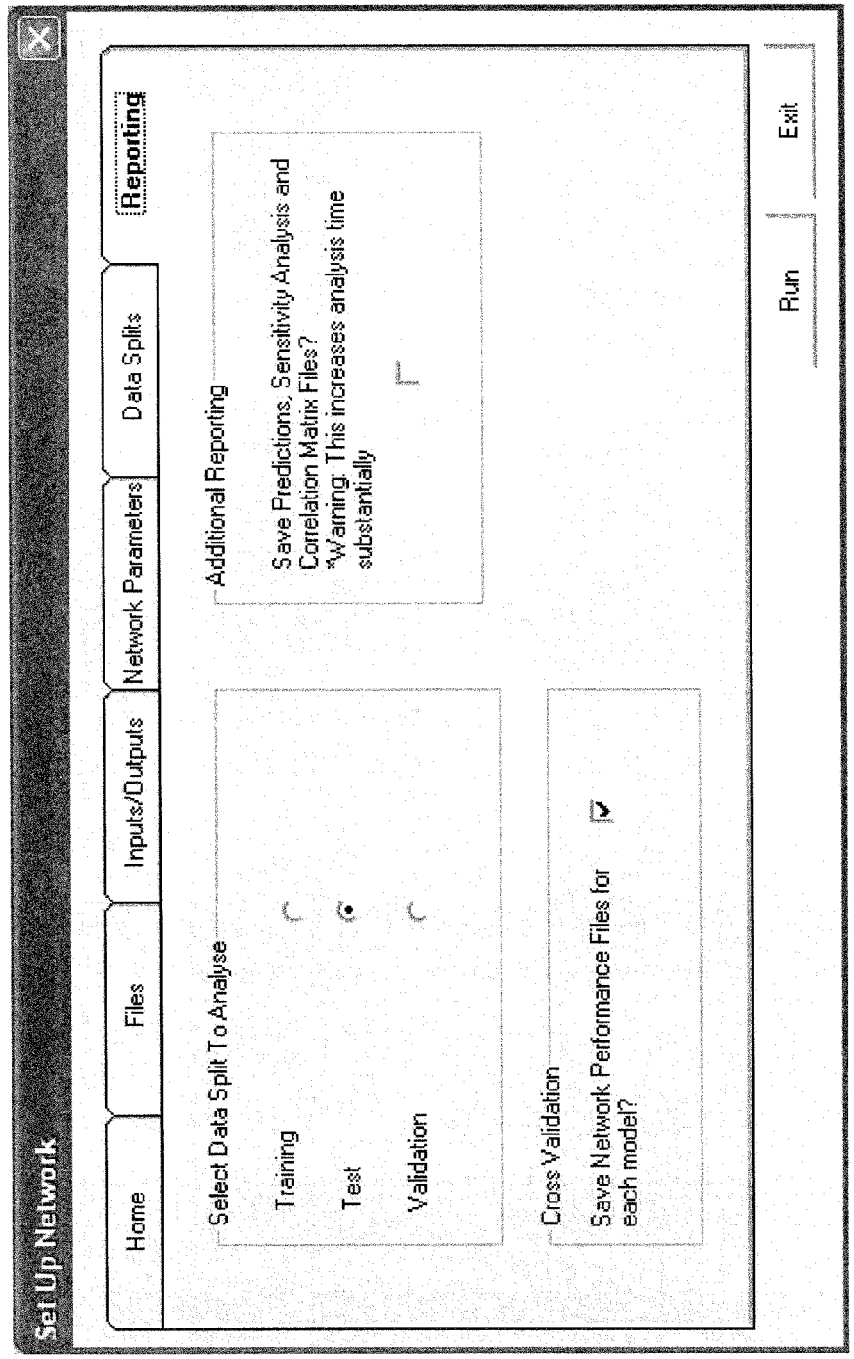

FIG. 5 is a flow chart illustrating the method of analysing the data set of FIG. 3 in accordance with an embodiment of the present invention.

In Step 40, the input and output variables to be used in the method of analysis are identified. In the example of the data set of FIG. 3, the input data will be gene expression data relating to a gene and the output data will be condition (i.e. healthy versus cancerous) data. It is noted that the output node will return a numerical output in the range "0" to "1" and the system may be set up such that "0" corresponds to healthy and "1" to cancer.

In Step 42, an input (i.e. a particular gene, for example gene C) is chosen as the input (input 1) to the ANN shown in FIG. 4.

In Step 44, the ANN is trained using random sample cross validation. In other words a subset of the overall dataset is used to train the neural network, a "training subset". In the context of the dataset of FIG. 3, this might mean that gene expression data for the chosen gene (gene C) from samples 1-3 and 8-10 is used to train the network. During this training phase the output condition (healthy versus cancer) from the network can be compared to the true condition.

In Step 46, the performance of the artificial neural network for input 1 is recorded and stored.

In Step 48, a further gene is chosen as the sole input to train the neural network and the system cycles round to Step 44 again so that the network is trained from its initial state again using this new data. For example, gene H might be the next input to be chosen and the gene expression data for gene H from samples 1-3 and 8-10 may then be used to train the network again.

Steps 44 and 46 are then repeated (indicated via arrow 50) for each input as sole input to the network (i.e. gene and its associated expression data in the example of FIG. 3) and the network performance is recorded for each input.

Once each input in the training subset has been used as input the system moves to Step 52 in which the various inputs are ranked according to the error from the true outcome and the best performing input is chosen.

In Step 54 the system moves onto train the network with a pair of inputs, one of which is the best performing input identified in Step 52 and the other is one of the remaining inputs from the training subset. The performance of the network with this pair of inputs is recorded.

The system then repeats this process with each of the remaining inputs from the training subset in turn (indicated via arrow 56), i.e. each of the remaining inputs is paired in turn with the best performing sole input identified in Step 48.

Once each of the remaining inputs has been used, the system identifies, in Step 58, the best performing pair of inputs.

The system then returns to Step 42 (indicated via arrow 60) and repeats the whole process, continually adding inputs until no further improvement in the performance of the artificial neural network is detected (Step 62). At this point, the artificial neural network has identified the inputs which are most closely related to the outcome. In the case of the gene/gene expression data example of FIG. 3, the system will have identified the genetic biomarkers for the dataset that point towards the development of cancer in the sampled individuals.

FIGS. 6a-c shows the development of the artificial neural network 20 through the first few cycles of the flow chart of FIG. 5. In FIG. 6a, the neural network is as shown in FIG. 4. A single input 28 is provided for the gene expression data related to input 1.

In FIG. 6b, the best performing single input has been chosen based on the performance on an unseen (by the model) validation set (Step 52) and the system has moved to testing the performance of input pairs. The number of nodes in the input layer has therefore increased to two nodes (28, 30). The number of nodes in the hidden layer is still constrained at two and the initial weights of the interconnections are similarly constrained (as per the set up of FIG. 4) in order to optimise the network performance.

In FIG. 6c, the best performing pair of inputs (comprising the best sole input from FIG. 6a plus one other input identified in FIG. 6b) has been chosen and the system has moved onto testing the performance of three inputs (28, 30, 32). The hidden node and initial weight configurations remain unchanged.

The addition of further input nodes continues until no further improvement in network performance is identified.

The ANN of the invention shows significant technical utility in analysing complex datasets generated from diverse sources. In one example of the invention in use, clinical data from cancer patients is analysed in order to determine diagnostic and prognostic genetic indicators of cancer. In another example of the invention in use, meteorological measurements are analysed in order to provide predictions of future weather patterns. The invention shows further utility in the fields of ocean current measurements, financial data analysis, epidemiology, climate change prediction, analysis of socio-economic data, and vehicle traffic movements, to name just a few areas.

Cancer Prediction:

Cancer is the second leading cause of death in the United States. An estimated 10.1 million Americans are living with a previous diagnosis of cancer. In 2002, over one million people were newly diagnosed with cancer in the United States (information from Centres for Disease Control and Prevention, 2004 and 2005, and National Cancer Institute, 2005). According to Cancer Research UK, in 2005 over 150,000 people died in the United Kingdom as a result of cancer. Detecting cancer at an early stage in the development of the disease is a key factor in enabling the disease to be effectively treated and prolonging the life of the affected individual. Cancer screening is an attempt to detect (undiagnosed) cancers in the population, so as to enable early therapeutic intervention. Screens for detecting and/or predicting cancer are advantageously suitable for testing large numbers of subjects; are affordable; safe; non-invasive; and accurate (i.e. exhibiting a low rate of false positives).

At present there are no clinically validated markers for metastatic melanoma. Data has been obtained from mass spectrometry (MS) proteomic profiling of human serum samples from patients with melanoma at various stages of disease. Using the stepwise ANN approaches of the present invention, protein ions have been identified that distinguish stage IV melanoma patients from healthy controls with an accuracy of over 90%. Using the same approach to analyse the proteomic profiles of digested peptides, ions were identified which predicted validation subsets of samples to an accuracy of 100%. The groups of ions identified here distinguish stage IV metastatic melanoma from healthy controls with incredibly high sensitivity and specificity. This is of even greater significance when it is appreciated that conventional S-100 ELISA typically results in a reported 20% 'false negative' rate in patients with detectable metastases by routine clinical and radiographic studies Potential serum protein melanoma biomarker ions by mass spectrometry using SELDI chips have been reported previously (Mien et al (2005) Serum proteomic fingerprinting discriminates between clinical stages and predicts disease progression in melanoma patients, J Clin Oncol, 23, 5088-5093) where a mass region around 11,700 Da provided a highly statistically significantly difference in intensity between stage I and stage IV melanoma samples. In an example of the invention, described in more detail below, a MALDI MS method was used to generate a more rapid data analysis with higher resolution. These data were subsequently subjected to stepwise ANN analysis and nine ions were identified that discriminated between melanoma stage IV and healthy control sera. This analysis by ANNs of serum proteins resulted in a median accuracy of 92% (inter-quartile range 89.4-94.8%) in discriminating between sera from stage IV melanoma and control patients. The top ion at m/z 12000 was able to discriminate between classes with a median predictive accuracy of 64% (inter-quartile range 58.7-69.2%). This ion is similar in mass to the biomarker ion of m/z 11700 reported using the SELDI technology also for stage IV metastatic cancer reported previously (Mian, et al., 2005). The difference may be attributed to the fact that this ion was found to be significant when used in discriminating between stage I melanoma versus stage IV patients whereas here the ion reported at m/z 12000 was identified when classifying between IV melanoma and unaffected healthy control individuals. Further, in the manuscript by Mian and colleagues (Mian, et al., 2005) predictive performance was based primarily on spectra obtained from Ciphergen SELDI chip platform which are associated with inherent low-resolution read-outs using low-resolution MS equipment whereas here protein biomarker detection was carried out using a higher resolution MALDI-MS analyzer, so the m/z value of 11700 may have some variation associated with it. Although both studies used ANNs the approaches applied were different; here novel stepwise analysis approaches were used which allow for the identification of individual mass ions with high predictive performance, whereas the SELDI analysis (Mian, et al., 2005) used larger mass ranges to identify regions of the profile which were important in discriminating between groups. Therefore it is important to consider different data mining techniques may elicit different markers with differing importance.

Bioinformatic sequence analysis of the six predictive peptides identified two peptide ions belonging to Alpha 1-acid glycoprotein (AGP) precursor 1/2 (AAG 1/2) which when used together in a predictive model could account for 95% (47/50) of the metastatic melanoma patients. Additionally, another of the peptide ions was identified and confirmed to be associated with complement C3 component. Both proteins have been previously associated with metastatic disease in other types of cancers (Djukanovic, D et al (2000) Comparison of S100 protein and MIA protein as serum marker for malignant melanoma, Anticancer Res, 20, 2203-2207). This further confirms the value of the approach taken in the present invention. Other studies have also shown that increased levels of AGP are found in cancer (for example see Duche, J. C. et al (2000) Expression of the genetic variants of human alpha-1-acid glycoprotein in cancer, Clin Biochem, 33, 197-202). AGP, a highly heterogeneous glycoprotein, is an acute-phase protein produced mainly in the liver. However, its physiological significance is not yet fully understood, and as such AGP would not represent an expected melanoma biomarker.

To further assess whether the method of the invention could also be carried over to the analysis of gene expression data, as opposed to proteomic data, two publicly available datasets were analysed in accordance with the invention. Both of these datasets are associated with breast cancer. The first was a dataset published by van't Veer and co-workers (van't Veer et al (2002) Gene expression profiling predicts clinical outcome of breast cancer, Nature, 415, 530-536) and the aims here were to identify subsets of genes which could accurately discriminate between patients who developed distant metastases within five years and those who did not. The initial analysis by van't Veer and colleagues (van't Veer, et al., 2002) used a form of unsupervised clustering and supervised classification whereby genes were selected by the correlation coefficient of expression with disease outcome. This approach led to the identification of a 70 gene classifier which predicted correctly disease outcome to an accuracy of 83%. The ANN stepwise approach of the present invention resulted in the identification of twenty genes which accurately predicted patient prognosis to a median accuracy of 100% for blind data over a number of random sample cross validation resampling events. Some of the genes which constitute this expression signature have previously been associated with cancer outcome. For example the first gene identified by our model was Carbonic Anhydrase IX, and was capable of predicting 70% of the samples correctly by itself. Carbonic Anhydrase IX (CA IX) has been suggested to be functionally involved in pathogenesis due to its increased expression and abnormal localization in colorectal tumors (Saarnio, J., et al (1998) Immunohistochemical study of colorectal tumors for expression of a novel transmembrane carbonic anhydrase, MN/CA IX, with potential value as a marker of cell proliferation, Am J Pathol, 153, 279-285). CA IX has also been suggested for use as a diagnostic biomarker due to its expression being related to cervical cell carcinomas (Liao, S. Y., et al. (1994) Identification of the MN antigen as a diagnostic biomarker of cervical intraepithelial squamous and glandular neoplasia and cervical carcinomas, Am J Pathol, 145, 598-609). Surprisingly, seven of the twenty genes identified as important by the ANN method of the invention represent expressed sequence tags (EST's) and the associated gene is therefore of unknown function. However, given their newfound predictive capability with regards to survival, further clinical analysis is now justified.

A further dataset was published by West et al. (West, M., et al. (2001) Predicting the clinical status of human breast cancer by using gene expression profiles, *Proc Natl Acad Sci USA*, 98, 11462-11467) and the ANN stepwise approach of the invention was applied to this dataset in order to identify groups of genes would accurately predict the estrogen receptor (ER) status and the lymph node (LN) status of the patient. The initial analysis by West and colleagues used regression models in order to calculate classification probabilities for the various outcomes. In their study, when analyzing ER status, a 100 gene classifier was identified which predicted 34 of the 38 samples used in the training set accurately and with confidence, and which performed well during cross-validation. Using the same approach, the authors identified a 100 gene classifier which could classify a training set of samples according to lymph node status for the samples used in the training set. However, this approach was less successful in predicting LN status during cross-validation, where all of the LN+ cases had estimated probabilities at approximately 0.5, indicating these predictions contained a great deal of uncertainty, possible due to high levels in variation in the expression profiles of these samples. Using the stepwise methodology of the present invention, two gene expression signatures were identified. The first discriminated 100% of the cases correctly with regards to whether they were positive or negative for ER, and the second predicted whether the tumour had spread to the axillary lymph node, again to an accuracy of 100%. The accuracies reported here are from multiple separate validation data splits, with samples treated as blind data over 50 models with random sample cross validation.

Clearly the stepwise ANN approach of the present invention provides significant advantages over the techniques used previously not only ion identifying biomarkers with improved predictive capability, but also in identifying novel biomarkers for use in diagnostic and prognostic cancer prediction.

Crop Yield Prediction

The algorithmic approach of the present invention could also be applied to prediction of the effect of stresses on the productivity of crops. The natural environment consists of many interacting factors over time that can have an influence on crop yield. These include climatic factors such as temperature, light and humidity; soil factors such as nutrients, pH, salinity, and available water; pollutants in the air, water and soil; pests and diseases. This is clearly a complex system with very large number of interacting factors occurring in different states over time. The factors are also non linear and may interact with one another. Within this context the ANN approach according to the present invention could be applied to deconvolute these interactions and their influence on crop productivity and thus forecast yield under a given set of conditions.

The advantage of the approach described here is that it could identify an optimal subset of parameters with which yield could be predicted. These parameters could aid in the application of crop management and yield optimisation.

The invention is further illustrated by the following non-limiting example.

Example

A computational approach was taken to analyze genomic data in order to identify genes, proteins or gene/protein signatures, which correspond to prognostic outcome in patients with cancer. Genotypic, and subsequently phenotypic traits determine cell behaviour and, in the case of cancer, govern the cells' susceptibility to treatment. Since tumour cells are genetically unstable, it was postulated that sub-populations of cells arise that assume a more aggressive phenotype, capable of satisfying the requirements necessary for invasion and metastasis. The detection of biomarkers indicative of tumour aggression should be apparent, and consequently their identification would be of considerable value for early disease diagnosis, prognosis and response to therapy.

The present inventors have developed a novel method for determination of the optimal genomic/proteomic signature for predicting cancer within a clinically realistic time period and not requiring excessive processing power. The approach utilises ANNs and involves sequentially selecting and adding input neurons to a network to identify an optimum cancer biomarker subset based on predictive performance and error, in a form similar to stepwise logistic regression.

Three datasets were used to test and validate method of the invention. The first interrogates human serum samples with varying stages of melanoma. The samples were analysed by MALDI-TOF MS at Nottingham Trent University (Nottingham, United Kingdom) from samples collected by the German Cancer Research Centre (DKFZ, Heidelberg, Germany). The remaining two datasets were publicly available datasets which both originated from gene expression data derived from breast cancer patients.

The first dataset was derived from MALDI MS analysis for melanoma serum samples. The aims here were to firstly compare healthy control patients with those suffering from melanoma at the four different clinical stages, I, II, III and IV, in order to identify biomarker ions indicative of stage. Secondly, adjacent stages were to be analysed comparatively in the aim of identifying potential biomarkers representative of disease progression. All developed models were then validated on a second set of sample profiles generated separately from the first. This dataset contained 24,000 variables per sample.

The second dataset, published by van't Veer et al. (van't Veer, et al., 2002), used microarray technology to analyse primary breast tumour tissue in relation to development of metastasis. The authors generated data by gene expression analysis in a cohort of 78 breast cancer patients, 34 of which developed distant metastases within five years, and 44 which remained disease free after at least five years. Each patient had 24,482 corresponding variables specifying the $Log_{10}$ expression ratio of a single known gene or expressed sequence tag (EST).

The third dataset publish by West et al. (West, et al., 2001) used microarray technology to firstly analyse primary breast tumors in relation to estrogen receptor (ER) state and secondly to assess whether the tumor had spread to the axillary lymph node (LN), providing information regarding metastatic state. This dataset consisted of 13 ER+/LN+ tumors, 12 ER−/LN+ tumors, 12 ER+/LN− tumors, and 12 ER−/LN− tumors, each sample having 7,129 corresponding gene expression values. The approach described here was then validated using a second dataset (Huang, et al., 2003) which was made available by the same group as the first, and contained a different population of patients, ran on a different microarray chip.

Stepwise Approach Methodology

Artificial Neural Network Architecture

The ANN modelling used a supervised learning approach, multi-layer perceptron architecture with a sigmoidal transfer function, where weights were updated by a back propagation algorithm. Learning rate and momentum were set at 0.1 and 0.5 respectively. Prior to training the data were scaled linearly between 0 and 1 using minimums and maximums. This architecture utilized two hidden nodes in a single hidden layer and initial weights were randomized between 0 and 1. This approach has been previously shown to be a successful method of highlighting the importance of key inputs within highly dimensional systems such as this, while producing generalized models with accurate predictions (Ball, et al., 2002)

Artificial Neural Network Model Development

The same approach was applied across all datasets, with the only differences being the number of samples and input variables. Here, as an example the methodology as applied to the van't Veer dataset will be described. Data from the microarray experiments was taken in its raw form. This consisted of 78 samples each with 24,482 corresponding variables specifying the expression ratio of each single gene. Prior to training each model the data was randomly divided into three subsets; 60% for training, 20% for testing (to assess model performance during the training process) and 20% for validation (to independently validate the model on previously unseen data). This process is known as random sample cross validation and enables the generation of confidence intervals for the predictions on a separate blind data set, thus producing robust, generalized models.

Initially, each gene from the microarray dataset was used as an individual input in a network, thus creating n (24,482) individual models. These n models were then trained over 50 randomly selected subsets and network predictions and mean squared error values for these predictions were calculated for each model with regards to the separate validation set. The inputs were ranked in ascending order based on the mean squared error values for blind data and the model which performed with the lowest error was selected for further training. Thus 1,224,100 models were trained and tested at each step of model development.

Next, each of the remaining inputs were then sequentially added to the previous best input, creating n−1 models each containing two inputs. Training was repeated and performance evaluated. The model which showed the best capabilities to model the data was then selected and the process repeated, creating n−2 models each containing three inputs. This process was repeated until no significant improvement was gained from the addition of further inputs resulting in a final model containing the gene expression signature which most accurately modeled the data.

This process requires the training and testing of potentially millions of models. To facilitate this, software to automate the procedure has been created using Microsoft Visual Basic. Here, the inputs are added automatically, selecting the best contender biomarkers at each step. FIGS. 7(a)-(g) shows the software design detailing the various options available for ANN design and analysis (It is noted that the screenshots of FIGS. 7(a) to 7(g) are indicative only and the actual layout may vary). The entire process for running the algorithm can be summarized below:

1. Identify input and output variables
2. Start with input 1 as the first input to the model, $input_1$
3. Train the ANN using random sample cross validation
4. Record network performance for $input_1$
5. Repeat steps 3 and 4 using all inputs; $input_2$ ... $input_3$ ... $input_4$ ... $input_n$ as sole inputs in the ANN model
6. Rank inputs in ascending order based on the error on the test data split to determine best performing input at this step, $input_i$
7. Repeat from step 2, using each input sequentially with $input_i$ in an ANN model
8. Determine the best performing input combination for this step This whole process was repeated from step 3, continually adding inputs until no improvement was gained from the addition of further inputs Results Analysis of Melanoma Dataset Analysis of Control and Stage IV Disease Samples: Protein and Peptide Data Because there are no confirmatory blood markers for metastatic melanoma, we sought to develop a validated, robust and reproducible MALDI MS methodology using the same stepwise ANN approach to profile serum protein and tryptically digested peptides. This was applied to data derived from MALDI MS analysis representing (i) protein and (ii) digested peptide data from the control and diseased samples. Various analyses were carried out on these datasets in order to identify biomarker ions indicative of the classes shown in Table 1.

TABLE 1

Summary of analyses conducted (i)

| Analysis | Class 1 | Class 2 |
| --- | --- | --- |
| Protein ion analysis 1 | Healthy Control | Stage IV melanoma |
| Tryptic peptide ion analysis 1 | Healthy Control | Stage IV melanoma |

Figure 8:
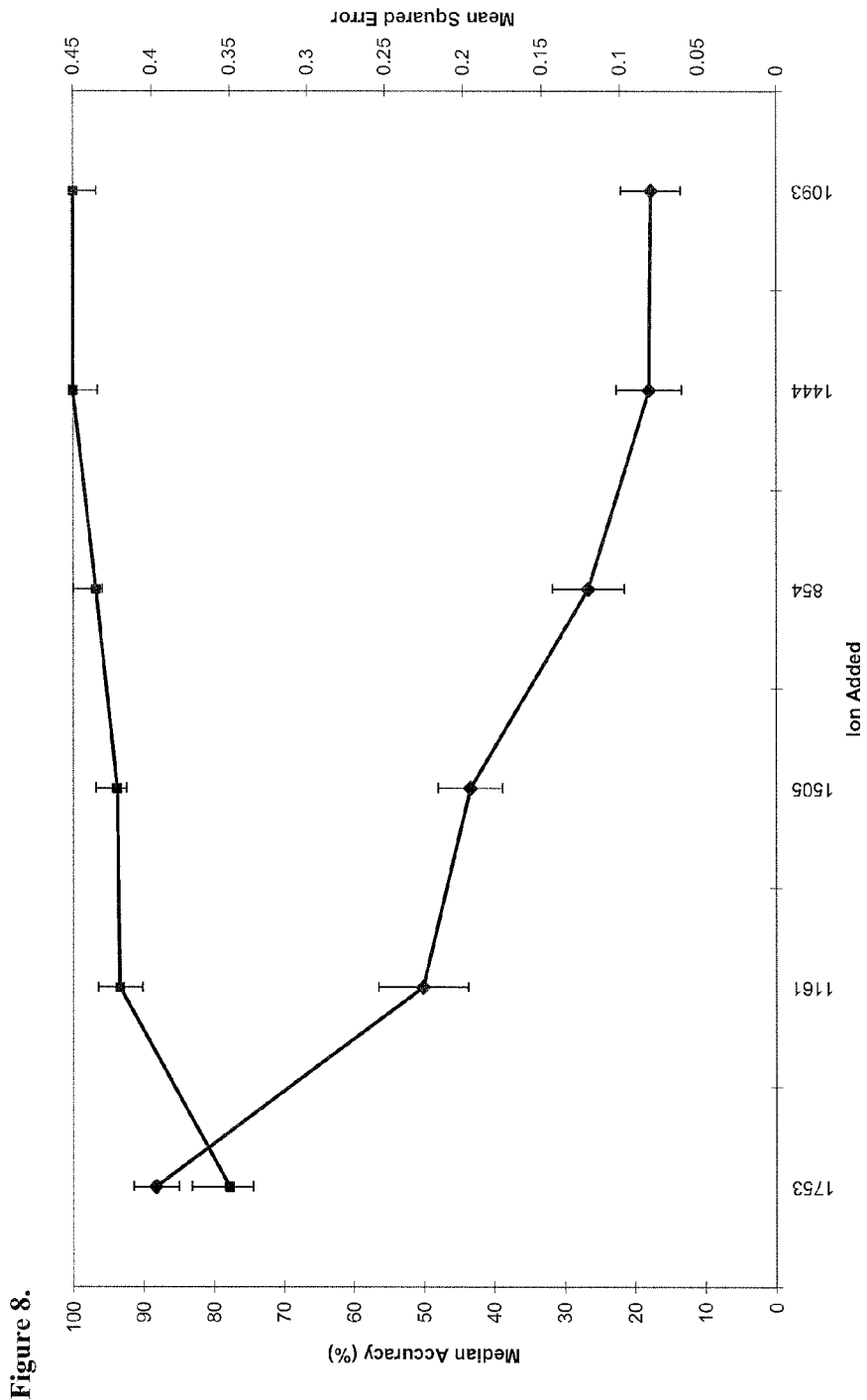
FIG. 8 is a graph showing the stepwise summary of ions added at each step of analysis of digested peptide data; Stage IV melanoma v Control. The line marked with ♦ points represents mean squared error value at each step with 95% confidence intervals being shown as error bars. The line marked with ■ points represents median model accuracy at each step of analysis with inter-quartile ranges being shown as error bars.

Biomarker patterns containing 9 ions from the protein data and 6 ions from the digested peptides were identified, which when used in combination correctly discriminated between control and Stage IV samples to a median accuracy of 92.3% (inter-quartile range 89.4-94.8%) and 100% (inter-quartile range 96.7-100%) respectively. Table 2a-b shows the performance for the models at each step of the analysis for the protein and peptide data. This shows that with the continual addition of key ions, an overall improvement in both the error associated with the predictive capabilities of the model for blind data, and also the median accuracies for samples correctly classified. Nine ions was determined to be the most effective subset of biomarker ions producing the best model performance for the protein data as no significant improvement was seen in predictive performance with the addition of further ions. No further steps were conducted beyond step 6 for the peptide data because after these step because no significant improvement in performance could be achieved. Therefore these models were considered to contain a subset of ions representing either the proteins or digested peptides, which most accurately modelled the data. FIG. 8 shows the error and performance progression for the peptide data when using the stepwise approach for biomarker identification.

TABLE 2a

Summary of stage IV vs control protein ions identified at each step of the analysis

| Step | Protein Ion | Median Accuracy (%) | Inter-Quartile Range |
|---|---|---|---|
| 1 | 12000 | 64.1 | 58.7-69.2 |
| 2 | 14847 | 73.2 | 69.8-75.8 |
| 3 | 1649 | 80.4 | 77.4-83.3 |
| 4 | 15477 | 80 | 77.9-84 |
| 5 | 13255 | 82.7 | 79.1-85.2 |
| 6 | 3031 | 83.8 | 79.8-86.1 |
| 7 | 4791 | 87 | 83.9-90.4 |
| 8 | 9913 | 86.6 | 83.2-89.8 |
| 9 | 4835 | 92.3 | 89.4-94.8 |
| 10 | 15269 | 90.4 | 87.2-92.6 |
| 11 | 2730 | 90.3 | 87.1-92.2 |
| 12 | 9919 | 90.4 | 87.3-92.5 |
| 13 | 9971 | 91.9 | 88.3-94 |
| 14 | 11735 | 90.4 | 87.1-92.5 |

TABLE 2b

Summary of stage IV vs control digested peptide ions identified at each step of the analysis

| Step | Peptide Ion | Median Accuracy (%) | Inter-Quartile Range |
|---|---|---|---|
| 1 | 1753 | 77.8 | 74.4-83.2 |
| 2 | 1161 | 93.3 | 90.2-96.4 |
| 3 | 1505 | 93.7 | 92.4-96.7 |
| 4 | 854 | 96.7 | 95.8-100 |
| 5 | 1444 | 100 | 96.5-100 |
| 6 | 1093 | 100 | 96.7-100 |

Analysis of Digested Peptide Data: Diseased Stages I, II, III and Control Samples Next, because the analysis of the peptide data provides the potential for subsequent protein identification, it was decided that these peptide MALDI MS profiles would be analysed in the search for differential biomarker ions which would be representative of firstly disease stage (by analysing the individual stages against control populations) and secondly disease progression (by generating predictive models classifying between adjacent disease stages). The analyses conducted in this part of the study are summarised in Table 3.

Figure 9:
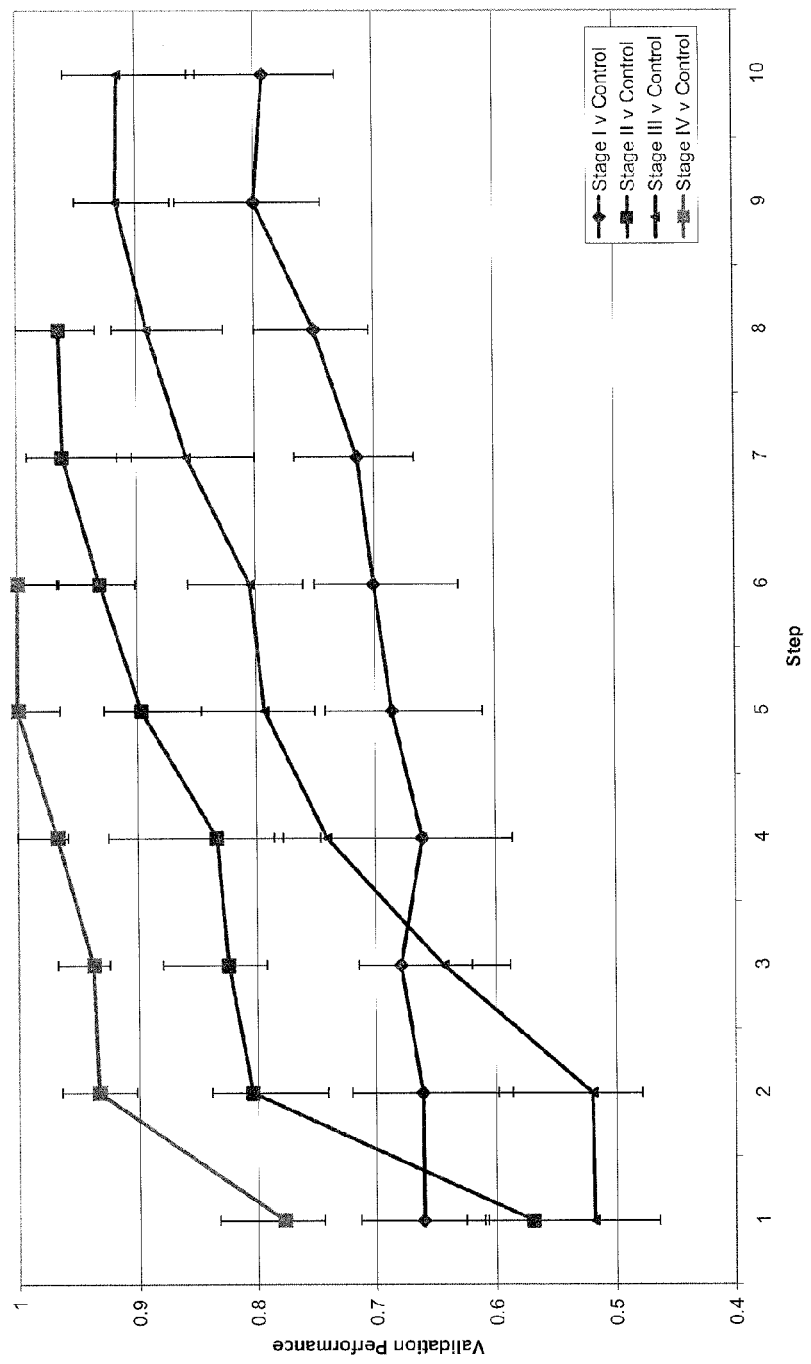
FIG. 9 is a graph showing an overall summary of stepwise model performance of diseased groups v control samples

Initially, in order to identify ions which were representative of disease stage, the stepwise approach was applied to identify subsets of biomarker ions which could predict between disease stage and control samples. This would therefore provide valuable information concerning which peptide ions were showing differential intensities that were specific to the disease stage of interest. Table 4 shows the biomarker subsets identified in each model, and their median performance when predicting validation subsets of data over 50 random sample cross validation resampling events. FIG. 9 shows the stepwise analysis summary across all of the models for each step of analysis. As expected, the models predicted stage I v control with the least accuracy (80%), suggesting that because early stage disease is a non-penetrating skin surface legion, changes occurring in the serum at the protein level are less significant than at advanced stages of disease. Nonetheless, the ability to predict incidence of stage I melanoma to accuracies of 80% using serum would be viewed as clinically significant. It was interesting to note that of the biomarker ions identified by this approach, in several instances the same ions were occurring across different models. Ions 1299 and 3430 (3432) were found to differentiate between both Stage I and Stage II disease vs control samples. Ions 1251 and 1283 (1285) were found to differentiate between Stage II and Stage III disease vs control, whilst ion 1753 (1754) was identified in both the Stage III and Stage IV diseased vs controlled models.

TABLE 3

Summary of analyses conducted.

| Analysis | Class 1 | Class 2 |
|---|---|---|
| Tryptic peptide ion analysis 2 | Healthy Control | Stage I melanoma |
| Tryptic peptide ion analysis 3 | Healthy Control | Stage II melanoma |
| Tryptic peptide ion analysis 4 | Healthy Control | Stage III melanoma |
| Tryptic peptide ion analysis 5 | Stage I melanoma | Stage II melanoma |
| Tryptic peptide ion analysis 6 | Stage II melanoma | Stage III melanoma |
| Tryptic peptide ion analysis 7 | Stage III melanoma | Stage IV melanoma |

Considering that 3500 individual ions are trained and tested at each step of analysis over 50 random sample cross validation resampling events, it seems unlikely that their consistent identification as the most important ions at a given step would be a consequence of chance, providing confidence that these ions are representing proteins which are showing a true change in intensity in patients with disease at differing stages.

Analysis of Adjacent Diseased Groups

Once biomarker ions representative of individual disease stage had been determined, it was decided important to analyse adjacent group stages of disease, which would potentially identify biomarker ions which would represent those responding differently as disease progressed, and would be predictive and indicative of disease stage. Table 5 shows the biomarker subsets identified in each model, and their median performance when predicting validation subsets of data over 50 random sample cross validation resampling events. It was interesting to find that subsets of ions could be identified which were able to predict between stages to extremely high accuracies; 98% for stage I v stage II and 100% for stage II v stage III and stage III v stage IV. Furthermore, only two peptide biomarker ions were required in order to perfectly discriminate between stage II and stage III, with one of these ions, 903, also being important in the classification of stage III v stage IV, suggesting that this ion is potentially of importance in disease progression to advanced stages, and appears to be downregulated as melanoma stage advances from stage II to IV, which could only be confirmed by further studies.

TABLE 4

Summary of overall results from digested peptide analysis. Stages I, II, III, and IV vs Control Peptide ions highlighted in bold represent ions corresponding to multiple groups.

| Dataset Modelled | Ions identified | Median Validation Performance (%) | Additional dataset performance |
|---|---|---|---|
| Stage I v Control | 864, 933, 980, 1299, 2309, 2886, 2966, 3220, 3430, 3489 | 80 | |
| Stage II v Control | 1251, 1283, 1299, 1968, 2244, 2411, 3432, 3443 | 96.5 | |
| Stage III v Control | 1251, 1285, 1312, 1371, 1754, 2624, 2715, 2999, 3161, 3326 | 91.7 | |
| Stage IV v Control | 854, 1093, 1161, 1444, 1505, 1753 | 100 | |

TABLE 5

Summary of overall results from digested peptide analysis.
Stages I, II, III, and IV vs Control Peptide ions highlighted in
bold represent ions corresponding to multiple groups.

| Dataset Modelled | Ions identified | Median Validation Performance (%) | Additional dataset performance |
|---|---|---|---|
| Stage I v Stage II | 1251, 1731, 1825, 1978, 2053 | 98 | |
| Stage II v Stage III | 861, 903 | 100 | |
| Stage III v Stage IV | 877, 903, 1625, 2064, 2754 | 100 | 93.4 |

Figure 10:
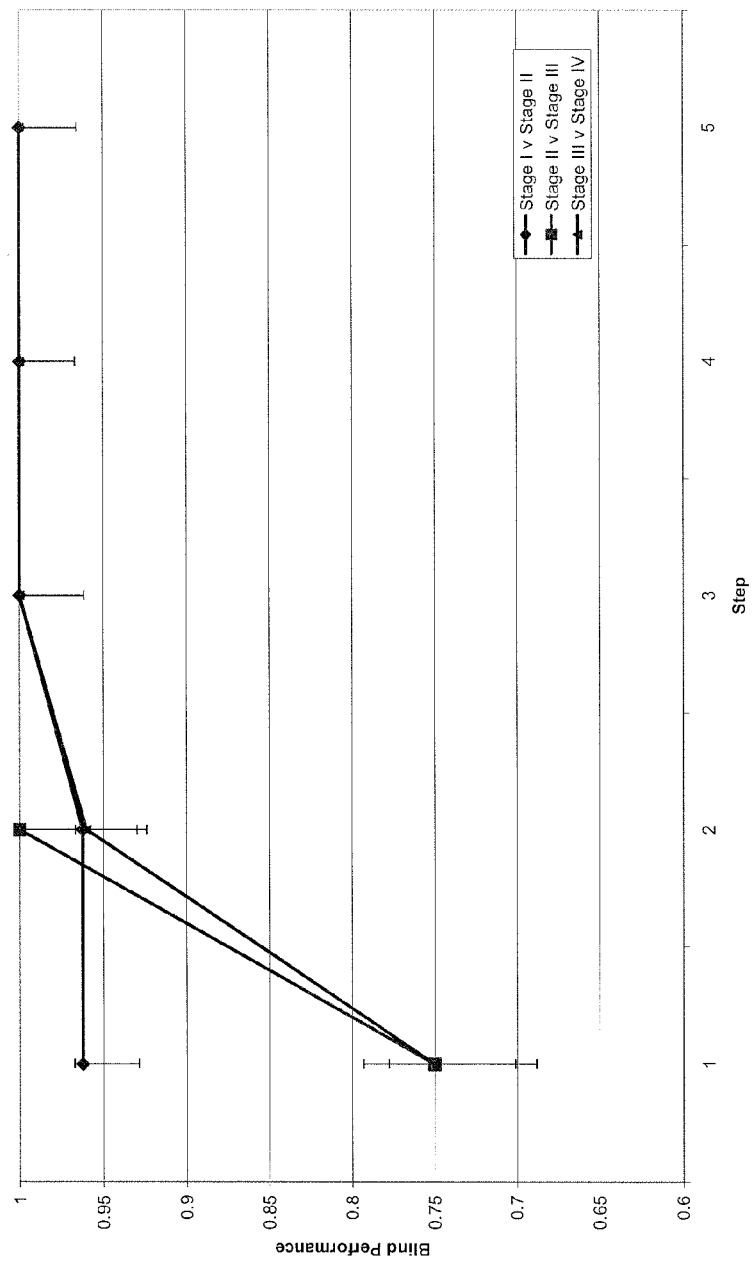
FIG. 10 is a graph showing a further overall summary of stepwise model performance of diseased groups v control samples FIG. 11 (a)-(c) are scatterplots showing principal components analysis using the biomarker ions identified by ANN stepwise approaches. Samples groups are differentiated by point style.
Figure 11A:
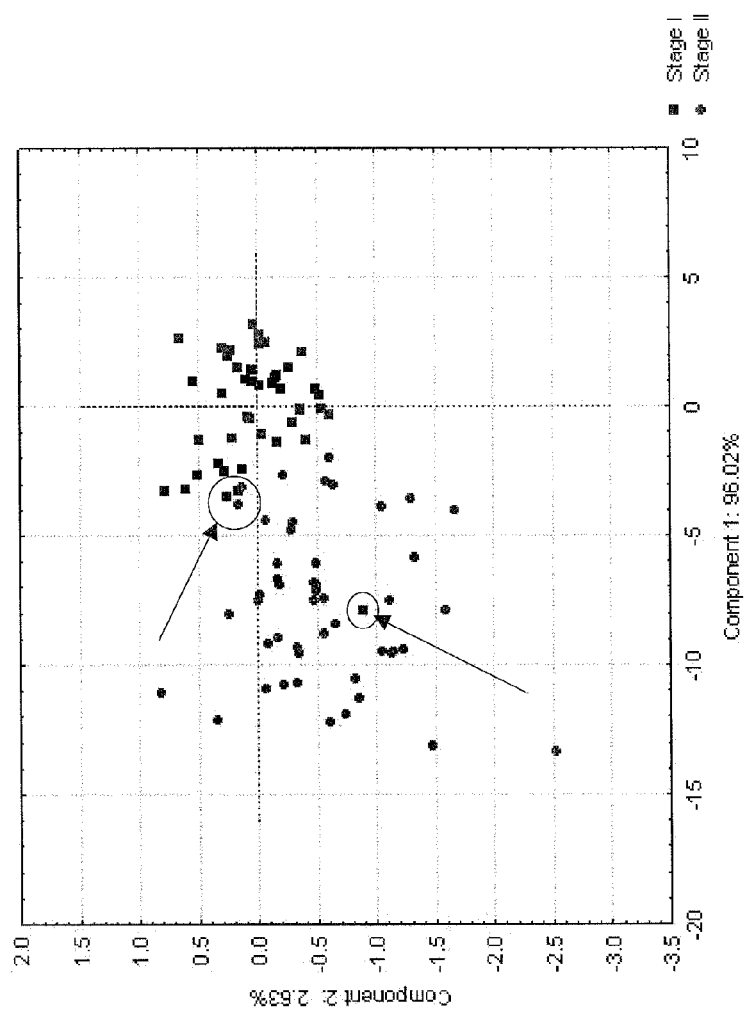
Figure 11B:
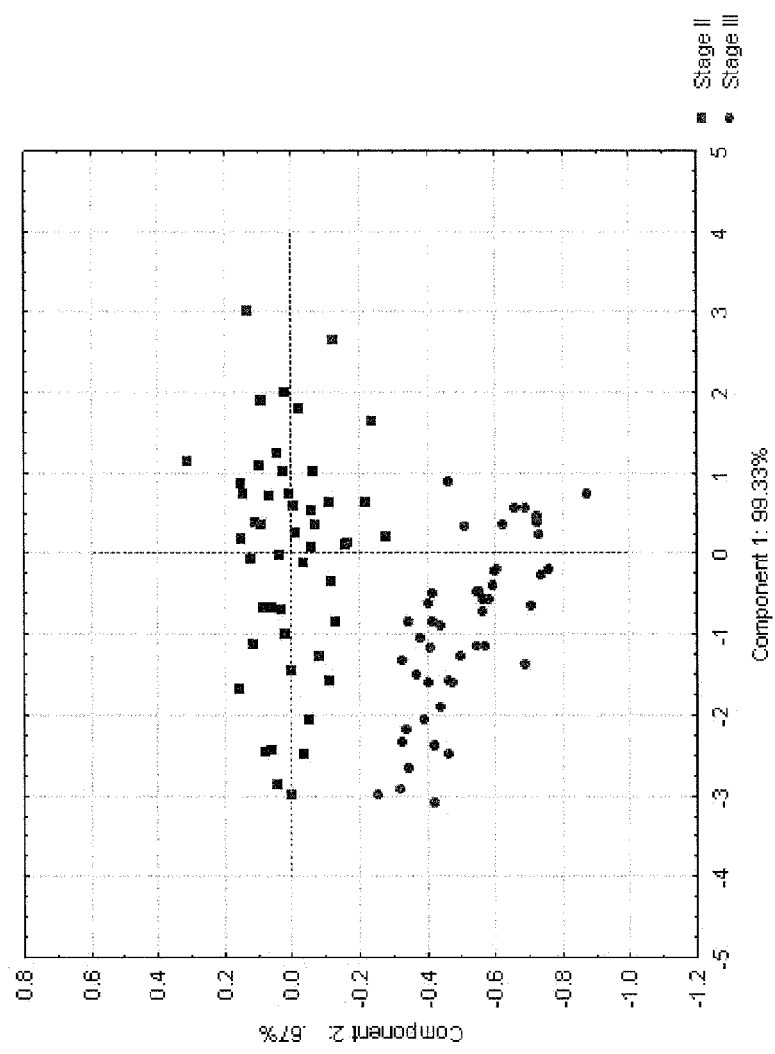
Figure 11C:
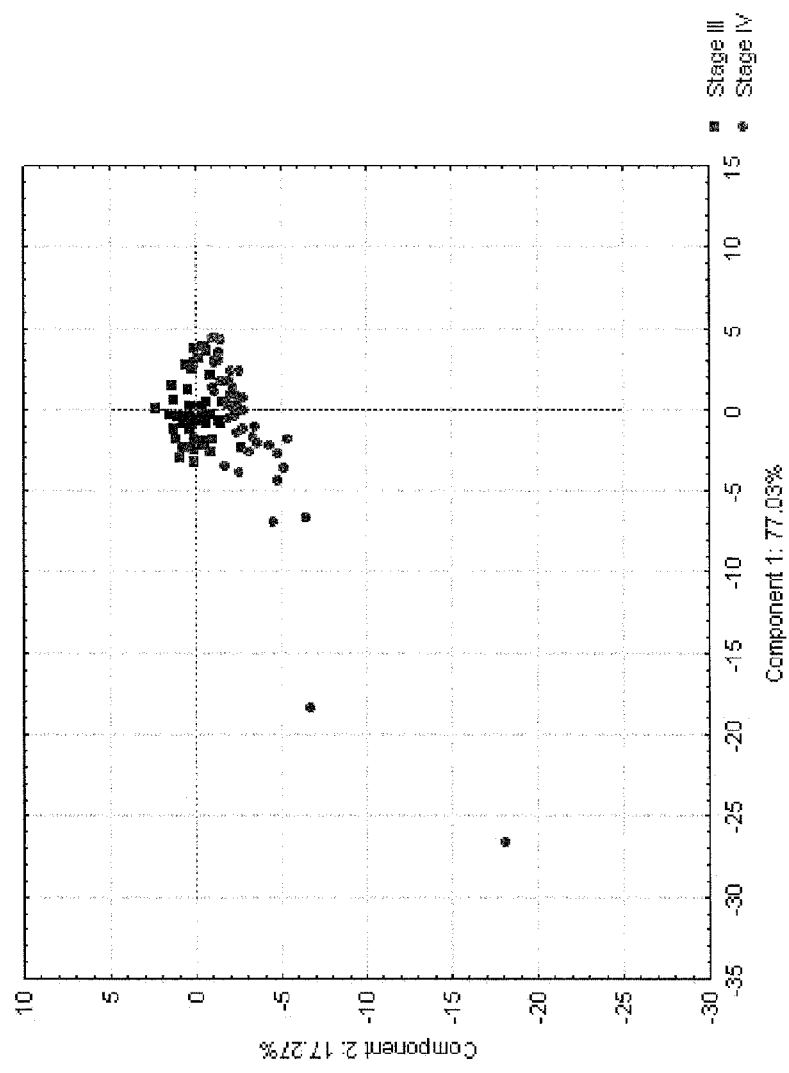
Figure 12:
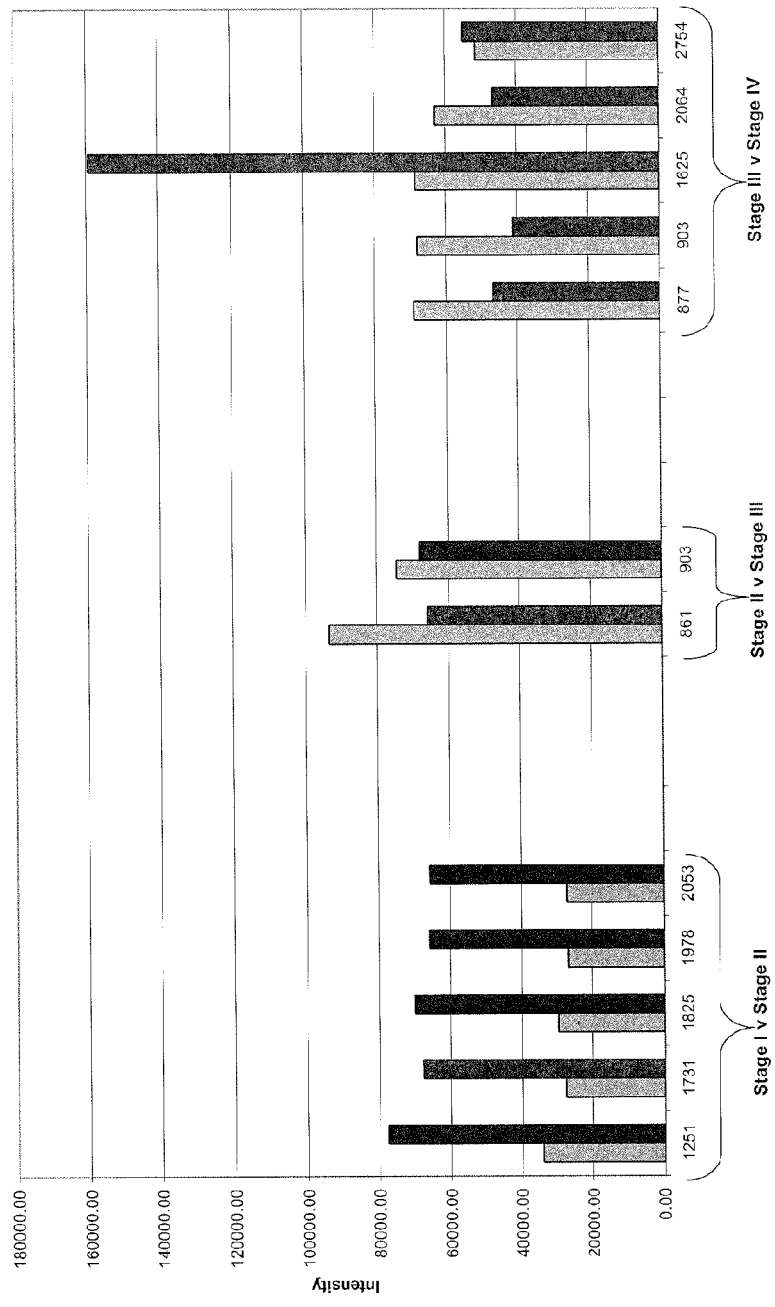
FIG. 12 is a bar graph showing mean group intensities of peptide biomarker ions identified by ANNs. All of the key biomarkers across the different stages are shown
Figure 13:
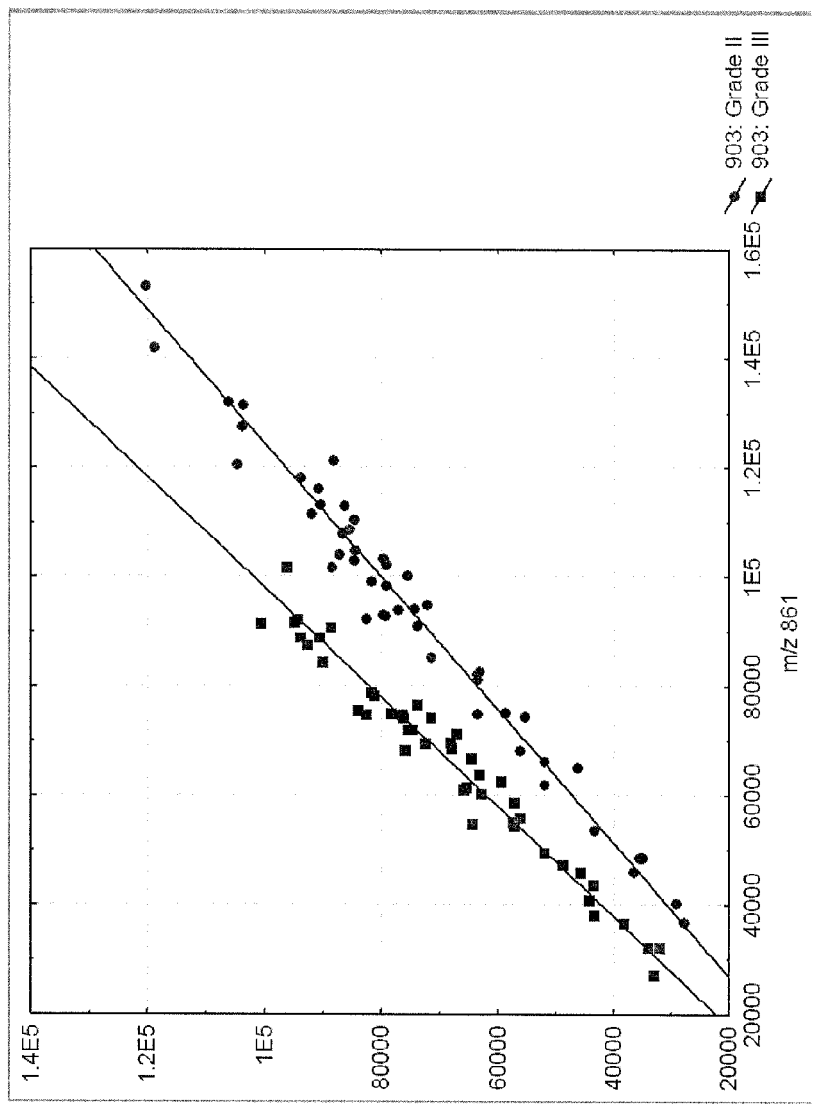
FIG. 13 is a scatterplot of ion 861 against ion 903 for Stage II and Stage III melanoma. Squares ■ indicate stage III samples, whilst circles ● show stage II samples.

The overall summaries for the stepwise analysis conducted here can be seen in FIG. 10. For visualization of the feature space that these samples are occupying, and to understand the decision surface that these models are generating, PCA was conducted using the subset of ions identified by the ANN stepwise approach. FIG. 11 (a)-(c) shows the PCA for the stage I v stage II, stage II v stage III and stage III v stage IV models respectively. It is evident that when using the biomarker ions identified by ANNs the samples can be separated into distinct clusters using PCA, with the clearest separation being with the stage II v stage III model. It is interesting to draw attention to the samples highlighted by arrows and circles in the stage I v stage II model (FIG. 11(a)). The first of these samples was identified as a stage I sample, but according to its profile PCA has placed it more indicative of stage II. Interestingly, the ANN model also predicted this sample as a stage II sample, suggesting it has strong features corresponding more to a stage II sample than a stage I sample which it was categorized as by the clinicians. Similarly, the region of samples highlighted on FIG. 11(b) which appear to be lying on the border of the decision surface were also predicted closely to the 0.5 decision threshold by the ANNs, again suggesting that these samples are showing characteristics of both classes according to their proteomic profiles. The relative closeness in feature space of the stage III and stage IV samples according to (FIG. 11(c)) suggests that the proteomic profiles of these samples are similar, and cannot be as clearly separated using the PCA as they are when using the ANN modelling, therefore requiring a non-linear decision surface to correctly classify this cohort of samples which are at a more advanced diseased stage. Furthermore, the mean group intensities of these ions has been analysed, with the summary being shown in FIG. 12. This shows how the biomarker ions identified as most important in the discrimination of sample groups has changed during the different stages of disease. It is clear from this that not all of these biomarker ions are being up regulated as disease progresses. All five of the ions identified in the stage I v stage II analysis show statistically significant ($p=<0.05$) increases in intensity. In the stage II v stage III model, both biomarker ions appear to be down regulated when disease is more advanced, with ion 861 significantly so. A scatterplot was produced of the two ions identified in this model, 861 an 903 (FIG. 13) and a clear separation of stage II and stage III samples is evident, with the stage III samples clearly showing lesser levels of ion 861. This enables one to derive a hypothetical decision boundary between the two classes. In the stage III v stage IV model, all ions (except for ion 2754) showed a significant increase or decrease in intensity as disease progressed, with ion 1625 showing a highly significant increase in intensity as disease progressed to stage IV.

Model Validation

To study the question of stability of this procedure over multiple experiments and to assess batch to batch reproducibility of the mass spectrometry analysis, both the proteins and peptides were run by the group on two separate occasions and the results of the second experiment were used to validate the stepwise methodology. This dataset was obtained by a different operator and on a different date. The second sample set was then passed through the developed ANN models to blindly classify them as a second order of blind data for class assignment. For the protein data, the model correctly classified 85% of these blind samples correctly, with sensitivity and specificity values of 82 and 88% respectively, with an AUC value of 0.9 when evaluated with a ROC curve. For peptides, the model correctly classified 43147 samples originating from control patients, and 43/43 samples from cancerous patients. This gave an overall model accuracy of 95.6%, with sensitivity and specificity values of 100 and 91.5% respectively, with AUC value of 0.98. This suggests that the peptide data was more reproducible than the protein data for this second batch of mass spectrometry analysis. The predictive peptide ions were subsequently sequenced and identified by colleagues using a variety of mass spectrometric techniques leading to the identification of two proteins; Alpha 1-acid glycoprotein (AGP) precursor 1/2 (AAG1/2) and complement C3 component.

Analysis of van't Veer et al. Dataset

The aims of the analysis were to utilise the novel stepwise ANN modelling approach of the invention in order to identify a gene expression signature which would accurately predict whether a patient would develop distant metastases within a five year time period, and thus identifying potential markers and giving an insight into disease aetiology. Following the rule of parsimony which suggests that the simplest model fitting the data should be used, an initial analysis was carried out using logistic regression (Subasi and Ercelebi (2005) Comput Methods Programs Biomed. 78(2):87-99). This method led to poor predictive performances with a median accuracy of just 53% (inter-quartile range 47-61%). With logistic regression, there is the potential disadvantage of autocorrelation between the large numbers of independent variables within the dataset, which is possibly the reason for the poor predictive performance suggesting that this dataset is not linearly separable.

Figure 14:
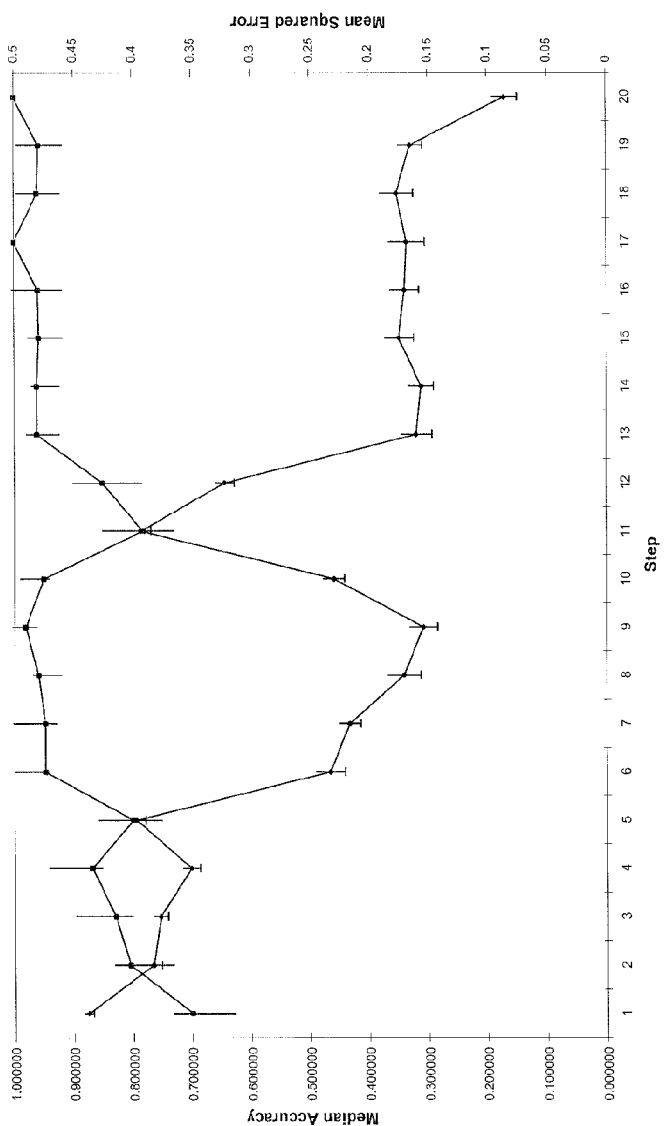
FIG. 14 is a graph showing model performance with each input addition over the course of the analysis. Line with ■ points represents median model accuracy with lower and upper inter-quartile ranges shown as error bars. The line with ♦ points shows the mean squared error for the predictions at each step with error bars indicating 95 confidence intervals.

The application of this approach resulted in the identification of a gene expression signature consisting of twenty genes which predicted patient prognosis to a median accuracy of 100% (inter-quartile range 100-100%, mean squared error of 0.085), where samples were treated as blind data over 50 models with random sample cross validation. The overall screening process assessed over ten million individual models. When evaluated with a ROC curve the model had an AUC value of 0.971 with sensitivity and specificity values of 98% and 94% respectively. FIG. 14 shows the performance for the models at each step of the analysis. It is evident that the continual addition of key genes leads to an overall improvement in the predictive capabilities of the model. The model showed a decrease in performance at steps 10 and 11 which may be due to a possible interaction between the genes present at these steps with one or more of the other genes in the model. After this point the model improved further still until step twenty, so this was considered to contain the genes which most accurately modelled the data. Further steps were not conducted because no significant improvement in performance could be achieved. A summary of the performances of the models at each step, together with the identity of the gene (where known) are given in Table 6.

TABLE 6

Summary of twenty genes used in the gene expression signature at each step of model development.

| Step | Gene Name | Gene Description | Median % Accuracy | Inter Quartile Range (%) | Mean Squared Error |
|---|---|---|---|---|---|
| 1 | CA9 | Carbonic anhydrase IX | 70 | 66.7-77 | 0.438 |
| 2 | | EST's | 80.5 | 77.7-87.7 | 0.383 |
| 3 | | ESTs, Weakly similar to RL17_HUMAN 60S RIBOSOMAL PROTEIN L17 [*H. sapiens*] | 83 | 76.1-85.9 | 0.377 |
| 4 | FLJ13409 | ESTs, Weakly similar to the KIAA0191 gene is expressed ubiquitously [*H. sapiens*] | 87 | 79.6-88.7 | 0.351 |
| 5 | LCHN | LCHN protein | 80 | 73.9-84.7 | 0.397 |
| 6 | TMEFF2 | Transmembrane protein with EGF-like and two follistatin-like domains 2 | 94.7 | 89.4-95.3 | 0.233 |
| 7 | HEC | Highly expressed in cancer, rich in leucine heptad repeats | 94.8 | 89.3-96.7 | 0.217 |
| 8 | HSPC333 | *Homo sapiens* HSPC337 mRNA, partial cds | 96 | 95-100 | 0.171 |
| 9 | | EST's | 98.1 | 94.6-100 | 0.154 |
| 10 | | *Homo sapiens* cDNA: FLJ22044 fis, clone HEP09141 | 95 | 90.9-95.9 | 0.23 |
| 11 | HUGT1 | UDP-glucose: glycoprotein glucosyltransferase 1 | 78.2 | 71.3-83.5 | 0.393 |
| 12 | LOC56899 | putative 47 kDa protein | 85.1 | 80-91.8 | 0.322 |
| 13 | DJ462O23.2 | Hypothetical protein dJ462O23.2 | 96.1 | 94.3-100 | 0.16 |
| 14 | HSU93243 | Ubc6p homolog | 96.1 | 95.2-100 | 0.155 |
| 15 | NRG2 | Neuregulin 2 | 95.8 | 94-100 | 0.174 |
| 16 | | EST's | 95.9 | 90.5-100 | 0.17 |
| 17 | | EST's | 100 | 95.4-100 | 0.168 |
| 18 | | EST's | 96.1 | 92.5-100 | 0.176 |
| 19 | NPHP1 | Nephronophthisis 1 (juvenile) | 95.8 | 92-100 | 0.165 |
| 20 | QDPR | Quinoid dihydropteridine reductase | 100 | 100-100 | 0.085 |

Median accuracy, lower and upper inter-quartile ranges, gene names (where known) and descriptions are shown.

To further validate the model, an additional set of 19 samples were selected, as in the original manuscript (van't Veer, et al., 2002). This set consisted of 7 patients who remained metastasis free, and 12 who developed metastases within five years. The 20 gene expression signature that had been identified correctly diagnosed all 19 samples correctly, further emphasising the present models' predictive power.

Analysis of West et al Dataset

The aims here were to identify a gene expression signature which would accurately predict between firstly estrogen receptor (ER) status, and secondly to determine whether it was possible to generate a robust model containing genes which would discriminate between patients based upon lymph node (LN) status. As before, an initial analysis was carried out using logistic regression which again led to poor predictive performances with a median accuracy of 78% (inter-quartile range 67-88%) for the ER data, and just 56% (inter-quartile range 44-67%) for the LN dataset, which is comparable to the predictions one would gain from using a random classifier.

Figure 15A:
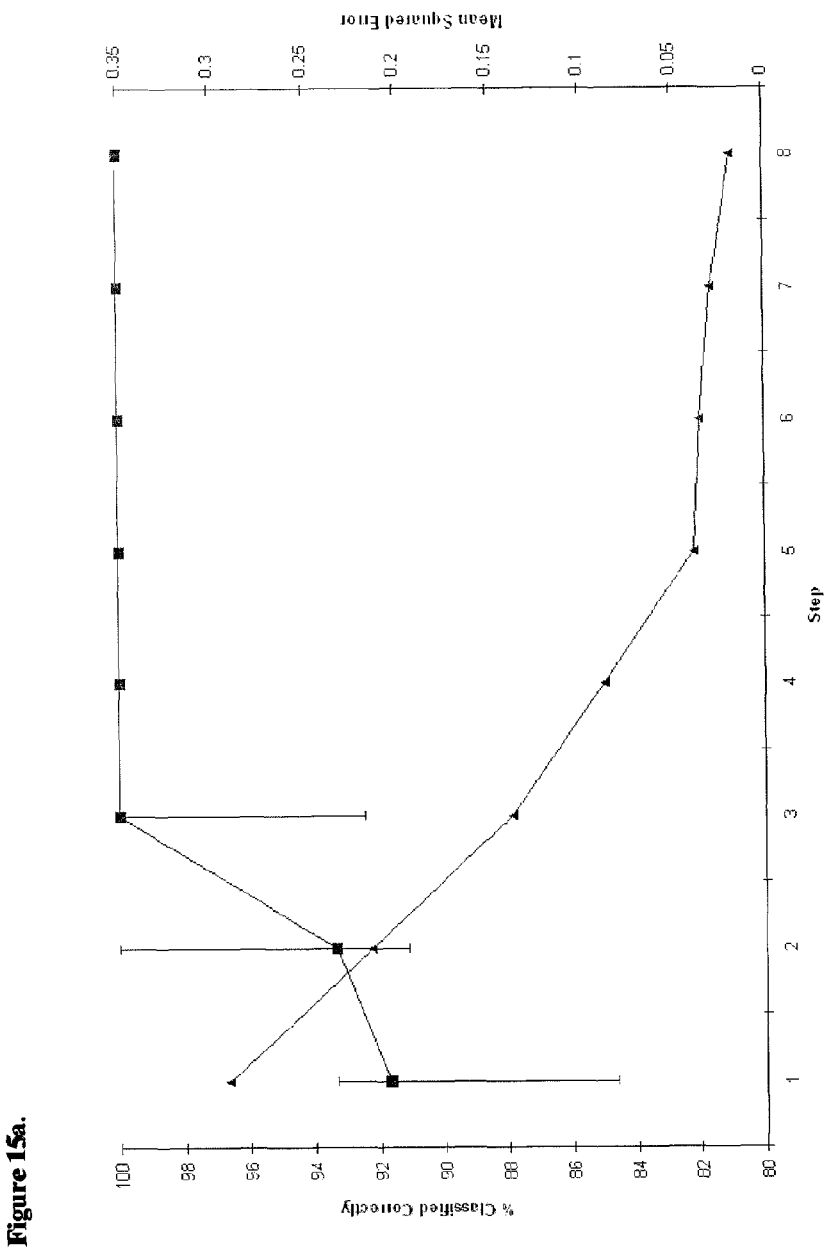
FIG. 15 (a)-(b) are graphs showing model performance with each input addition over the course of the analysis for (a) estrogen receptor (ER) status and (b) lymph node (LN) status. Line with ■ points represent median model accuracy with lower and upper inter-quartile ranges shown as error bars. Line with ▲ points shows the mean squared error for the predictions at each step with error bars indicating 95% confidence intervals FIG. 16 (a)-(b) are graphs showing a summary of stepwise analysis for the top ten genes identified at step 1 for (a) ER and (b) LN status.
Figure 15B:
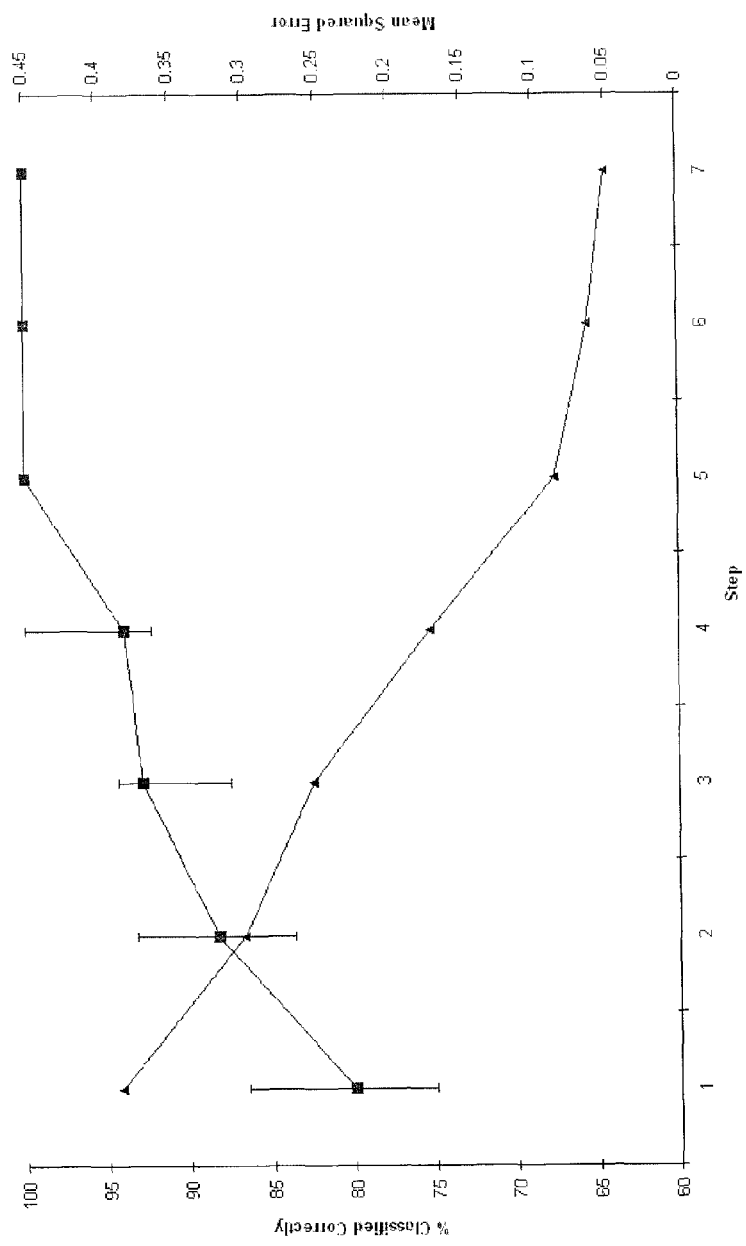

Here, using the stepwise methodology, two gene expression signatures were identified. The first discriminated 100% of the cases correctly with regards to whether they were positive or negative for ER, and the second predicted whether metastasis of the tumour to the axillary lymph node had occurred, to an accuracy of 100%. Again, the accuracies reported are from separate validation data splits, with samples treated as blind data over 50 models with random sample cross validation. The overall screening process assessed over five million individual models. When evaluated with a ROC curve the model had an area under the curve value of 1.0 with sensitivity and specificity values of 100% and 100% respectively for both ER and LN status. FIG. 15(a)-(b) shows the performance for the models at each step of the analysis. It is evident that the continual addition of key genes leads to an overall improvement in the error associated with the predictive capabilities of the model for blind data. After steps 8 and 7 for the ER and LN data respectively, no further steps were conducted because no significant improvement in performance could be achieved, therefore these models were considered to contain the genes which most accurately modelled the data. A summary of the performances of the models at each step, together with the identity of these are given in Table 7 a-b.

The models developed using the gene subsets identified by the approach described were applied to 88 samples from Huang and colleagues (Huang, et al (2003) Lancet, 361, 1590-1596). These samples were then subjected to classification based upon ER and LN status as with the first dataset. 88.6% of the samples could be classified correctly based on ER status, with a sensitivity and specificity of 90.4 and 80% respectively. 83% of samples were correctly classified based upon their LN status, with a sensitivity of 86.7% and specificity of 80%. The ROC curves AUC values were 0.874 and 0.812 for the ER and LN gene subset models respectively. It was expected that the predictive accuracies would be reduced when the models were applied to this additional dataset, but the accuracies reported here remain extremely encouraging because of the larger sample size, the differences in sample characteristics and microarray analysis described above. The ability to predict ER status at a higher rate than that of LN status suggests that there is a greater level of variation in the gene expression profiles with respect to LN status compared to that of ER.

Table 7a-b. Summary Genes Used in the Gene Expression Signature at Each Step of Model Development for (a) ER Status and (b) LN Status.

(a)

| Step | Gene Accession Number | Gene Description | Median % Accuracy | Inter Quartile Range (%) | Mean Squared Error |
|---|---|---|---|---|---|
| 1 | X58072-at | Human hGATA3 mRNA | 91.7 | 84.6-93.3 | 0.291 |
| 2 | Z29083-at | *H. sapiens* 5T4 gene for 5T4 Oncofetal antigen | 93.3 | 91.1-100 | 0.214 |
| 3 | M81758-at | SkM1 mRNA | 100 | 92.4-100 | 0.138 |
| 4 | M60748-at | Human histone H1 (H1F4) gene | 100 | 100-100 | 0.087 |
| 5 | M74093-at | Human cyclin mRNA | 100 | 100-100 | 0.038 |
| 6 | U22029-f-at | Human cytochrome P450 mRNA | 100 | 100-100 | 0.034 |
| 7 | U96131-at | *Homo sapiens* HPV16 E1 | 100 | 100-100 | 0.028 |
| 8 | M96982-at | *Homo sapiens* U2 snRNP auxiliary factor small subunit | 100 | 100-100 | 0.017 |

Median accuracy, lower and upper inter-quartile ranges, gene accession numbers, gene descriptions are shown.

(b)

| Step | Gene Accession Number | Gene Description | Median % Accuracy | inter Quartile Range (%) | Mean Squared Error | Response |
|---|---|---|---|---|---|---|
| 1 | AFFX-CreX-3-st | Bacteriophage P1 cre recombinase | 80 | 75-86.4 | 0.384 | † |
| 2 | M83221-at | *Homo sapiens* I-Rel mRNA | 88.2 | 83.7-93.2 | 0.301 | * |
| 3 | S79862-s-at | PSMD5 | 92.9 | 87.5-94.4 | 0.252 | ‡ |
| 4 | U39817-at | Human Bloom syndrome protein (BLM) mRNA | 94 | 92.3-100 | 0.172 | † |
| 5 | U63139-at | Human Rad50 mRNA | 100 | 100-100 | 0.085 | † |
| 6 | M83652-s-at | *Homo sapiens* complement component properdin mRNA | 100 | 100-100 | 0.062 | † |
| 7 | U30894-at | Human N-sulphoglucosamine sulphohydrolase (SGSH) mRNA | 100 | 100-100 | 0.05 | † |

Median accuracy, lower and upper inter-quartile ranges, gene accession numbers, gene descriptions are shown.

Identification of Multiple Biomarker Subsets

The stepwise methodology described above facilitates the identification of subsets of biomarkers which can accurately model and predict sample class for a given complex dataset. In order to facilitate a more rapid biomarker subset analysis, the stepwise approach described adds only the best performing biomarker each step of analysis. Although this appears to be an extremely robust method of biomarker identification, the question remains as to whether there are additional subsets of biomarkers existing within the dataset, which are also capable of predicting class to high accuracies. If this is true, then this would lead to a further understanding of the system being modelled, and if multiple biomarkers were to appear in more than one model subset, then this would further validate their identification, and enhance the potential of their role in disease status warranting further investigation.

To achieve these aims, the same West dataset was used as previously (West, et al., 2001). As can be seen from table 8a-b, in addition to the number one ranked biomarker at step one (which was subsequently used as the basis for the gene biomarker signature described earlier), there are several other potential candidate biomarkers which by themselves are able to classify a significant proportion of the sample population into their respective classes. Therefore an individual stepwise analysis was conducted on each of the remaining top ten genes identified in step one of the analysis, for both ER and LN status.

Results
Table 8a-b. Summary of Step 1 Analysis for (a) ER and (b) LN Status.

Table shows the gene identification and respective predictive performances of the top 10 ranked genes identified at step 1 of the analysis.

(a)

| Rank | Gene ID | Blind Performance |
|---|---|---|
| 1 | GATA3 | 89.8 |
| 2 | ESR1 | 87.6 |
| 3 | SLC39A6 | 85.5 |
| 4 | EST | 85.3 |
| 5 | HSD17B4 | 83.3 |
| 6 | EST | 84.2 |
| 7 | AR | 83.0 |
| 8 | LAD1 | 84.0 |
| 9 | SCNN1A | 84.2 |
| 10 | MAPT | 80.2 |

(b)

| Rank | Gene ID | Blind Performance |
|---|---|---|
| 1 | EST | 80.4 |
| 2 | GYPA/B | 70.9 |
| 3 | BLM | 71.2 |
| 4 | ACVR1B | 70.4 |
| 5 | EST | 64.3 |
| 6 | WNT5A | 66.7 |
| 7 | RELB | 61.3 |
| 8 | GK | 64.1 |
| 9 | PDE4B | 64.3 |
| 10 | TLE1 | 64.7 |

Figure 16A:
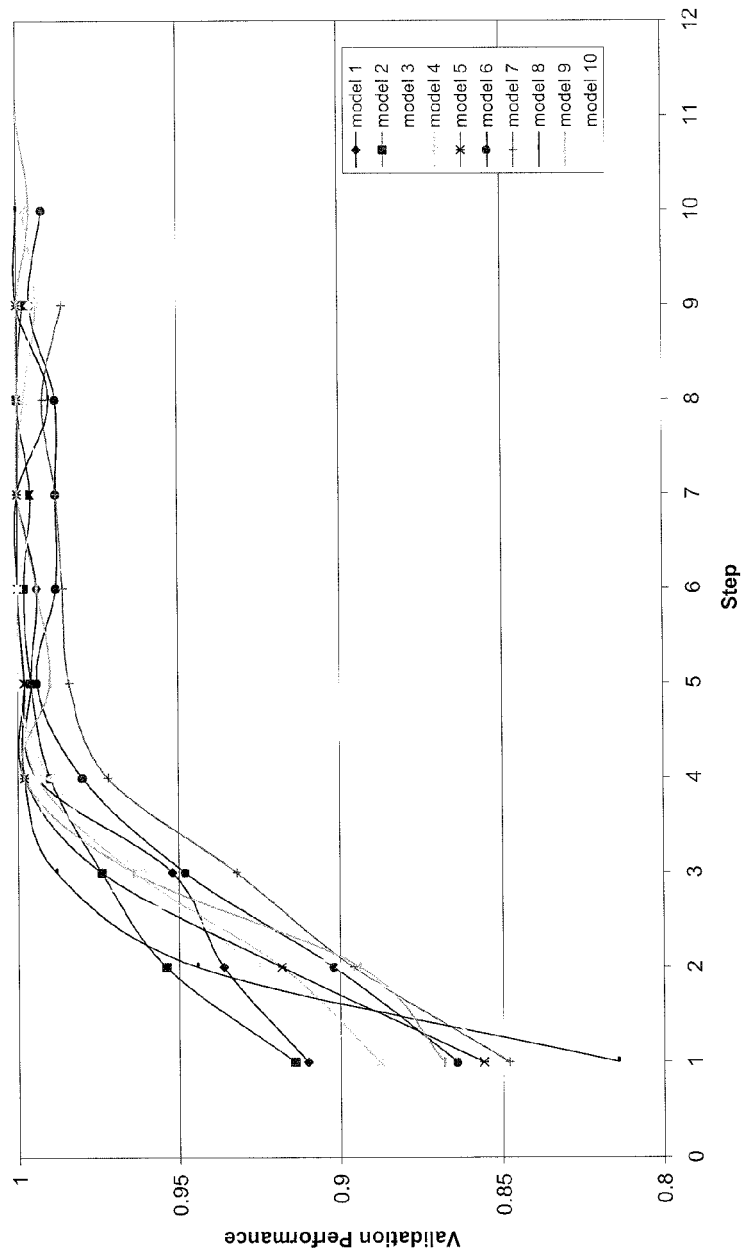
Figure 16B:
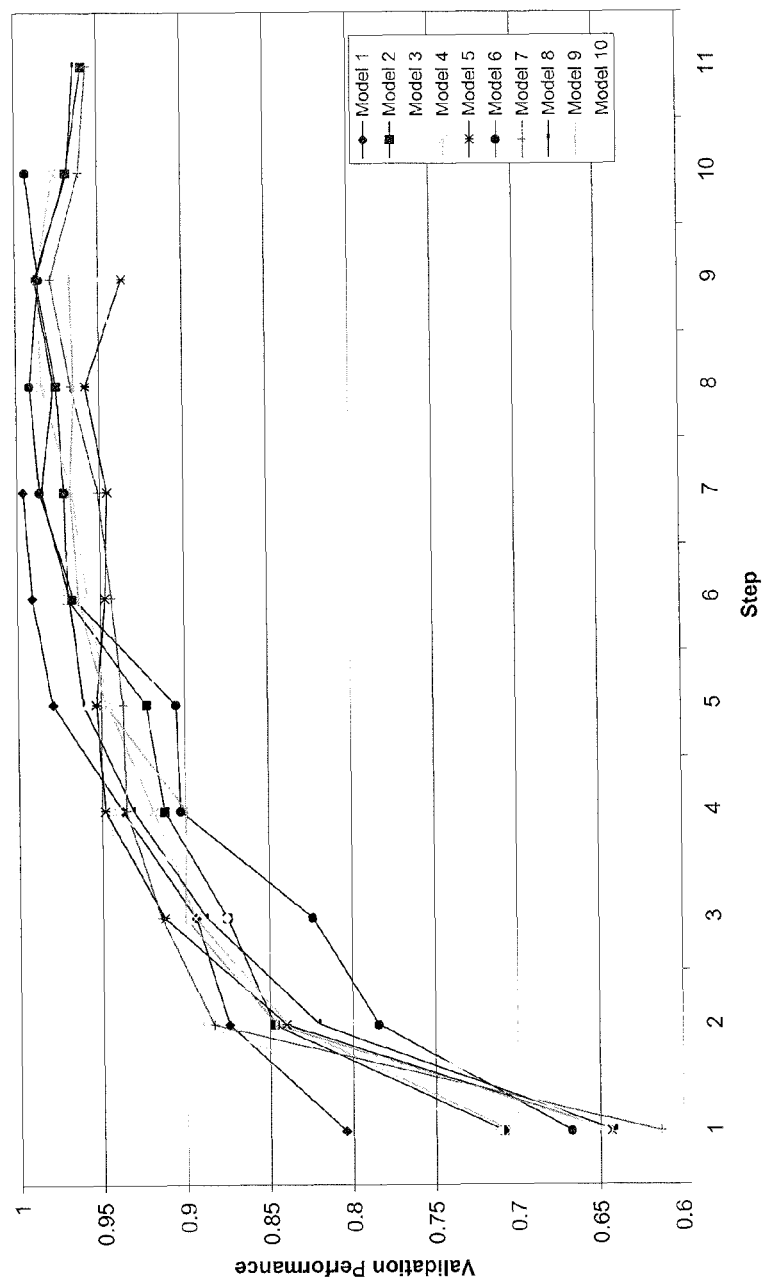

FIG. 16(a)-(b) shows the network performance at each step of analysis for all of these genes for (a) ER and (b) LN status. It is evident that all of these subsets have the ability to predict for blind subsets of samples to extremely high accuracies, with no significant differences between individual models. This suggests that there may be multiple genes acting in response to disease status, subsequently altering various pathways and altering the expression levels of many other genes. It is worthwhile to note that some of these genes were identified in many of the models (Table 9), for example an EST appeared in seven out of ten models, further highlighting its potential importance in LN status. This shows that there is not necessarily just one set of biomarkers which are correlates of a particular disease status of interest, but there may be many, and when one particular subset of biomarkers are affected in such a way that is indicative of disease status, then this may consequently have a cascade affect on many other biomarkers, altering their expression in a similar fashion.

Table 9. Summary of Genes Identified in Multiple Stepwise Modelling which Occur in More than One Model in (a) ER and (b) LN Status (a)

| Gene ID | Actual Gene Name | Number of Occurrences |
|---|---|---|
| CYP2B6 | Cytochrome p450 polypeptide 6 | 3 |
| CTSC | Cathepsin c | 3 |
| GATA3 | Gata binding protein 3 | 2 |
| EST | EST | 2 |
| CYP2A7 | Cytochrome p450 polypeptide 7 | 2 |

-continued (a)

| Gene ID | Actual Gene Name | Number of Occurrences |
|---|---|---|
| LRRC17 | Leucine rich repeat | 2 |
| NFKBIE | Nuclear factor of kappa | 2 |
| COX6C | Cytochrome c oxidase | 2 |
| HLF | Hepatic leukemia factor | 2 |
| IGLC | Immunoglobulin lambda | 2 |
| ZBTB16 | Zinc finger | 2 |
| RTN1 | Reticulon 1 | 2 |

(b)

| Gene ID | Actual Gene Name | Number of Occurrences |
|---|---|---|
| EST | EST | 7 |
| BLM | Bloom syndrome | 6 |
| ACVR1B | Activin a receptor | 4 |
| GYPA/GYPB | Glycophorin a/b | 3 |
| AXIN1 | Axin 1 | 3 |
| RELB | V-rel reticuloendotheliosis viral oncogene homolog b | 2 |
| PSMD5 | Proteasome (prosome, macropain) | 2 |
| SGSH | N-sulfoglucosamine sulfohydrolase (sulfamidase) | 2 |
| CTSH | Cathepsin h | 2 |
| NUP88 | Nucleoporin 88 kda | 2 |
| ENG | Endoglin | 2 |
| SYBL1 | Synaptobrevin-like 1 | 2 |

Stepwise Analysis Validation

To provide further evidence and confidence that the biomarker subsets identified in all of the above analyses by the stepwise approach were not random as a consequence of the high dimensionality of the datasets, two validation exercises were conducted. Firstly, ten inputs were randomly selected from the datasets and trained over 50 random sample cross validation events in an ANN model identically as for the stepwise method. This process was repeated 1,000 times, and the summary results are presented in Table 10.

Figure 17:
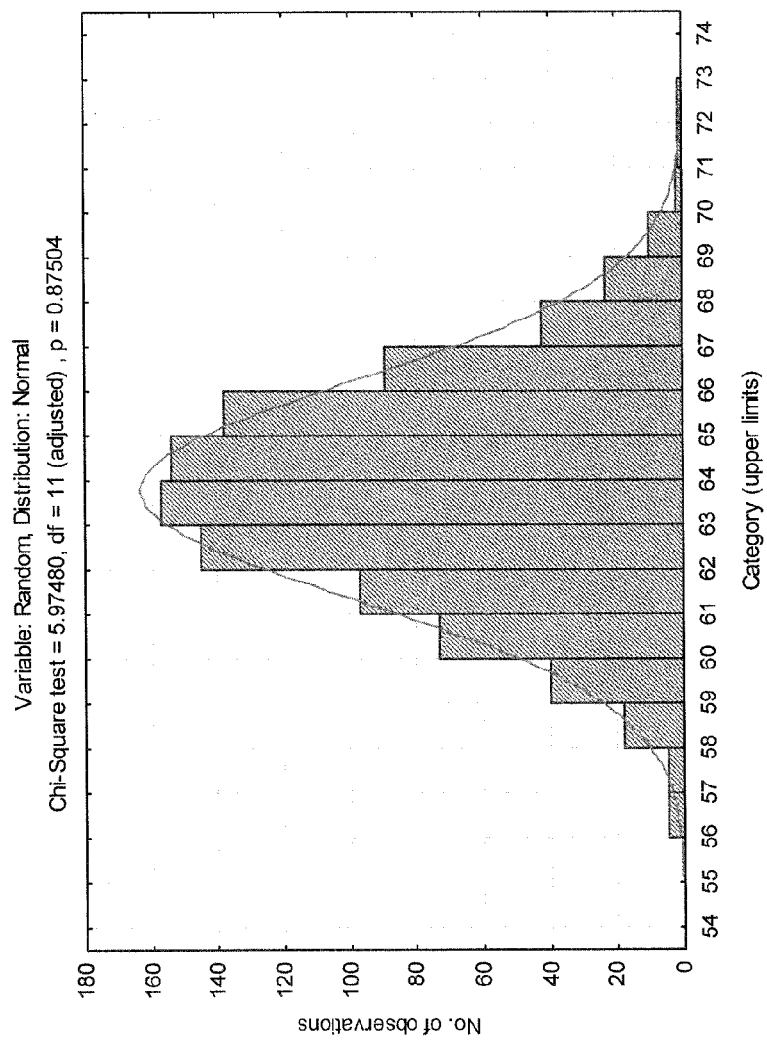
FIG. 17 is a graph showing the normal distribution of randomly generated models.

It is clear from Table 10 that the variation amongst models generated with these random input subsets is small, suggesting that a randomly generated model is able to predict sample class to accuracies in the region of 64% for blind data. These models will very rarely predict significantly higher than this value, which is highlighted in FIG. 17, which details the distribution of the model performance across the various models. The data follows a normal distribution, and therefore it is unlikely that a random model would generate a subset of inputs capable of very high classification accuracies, indicating that the stepwise ANN approach to modelling described here is selecting inputs which are discriminating between the groups of interest in a biologically relevant manner.

Figure 18A:
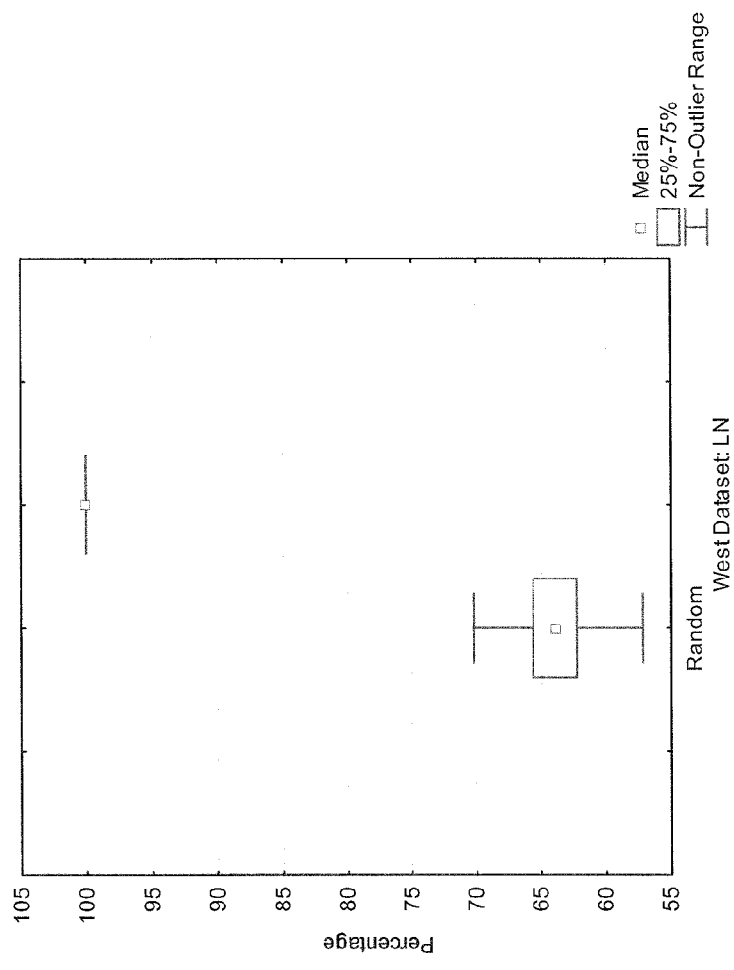
FIG. 18 (a)-(c) are box graphs showing comparison of performance of a random model to those generated with the stepwise approach of the invention.
Figure 18B:
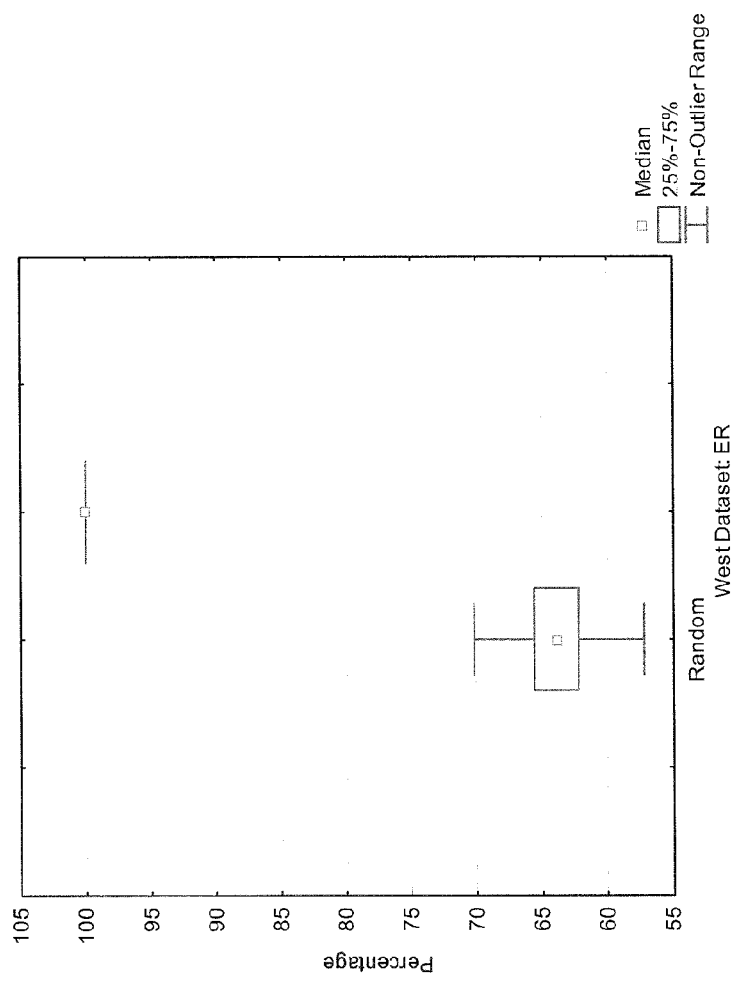
Figure 18C:
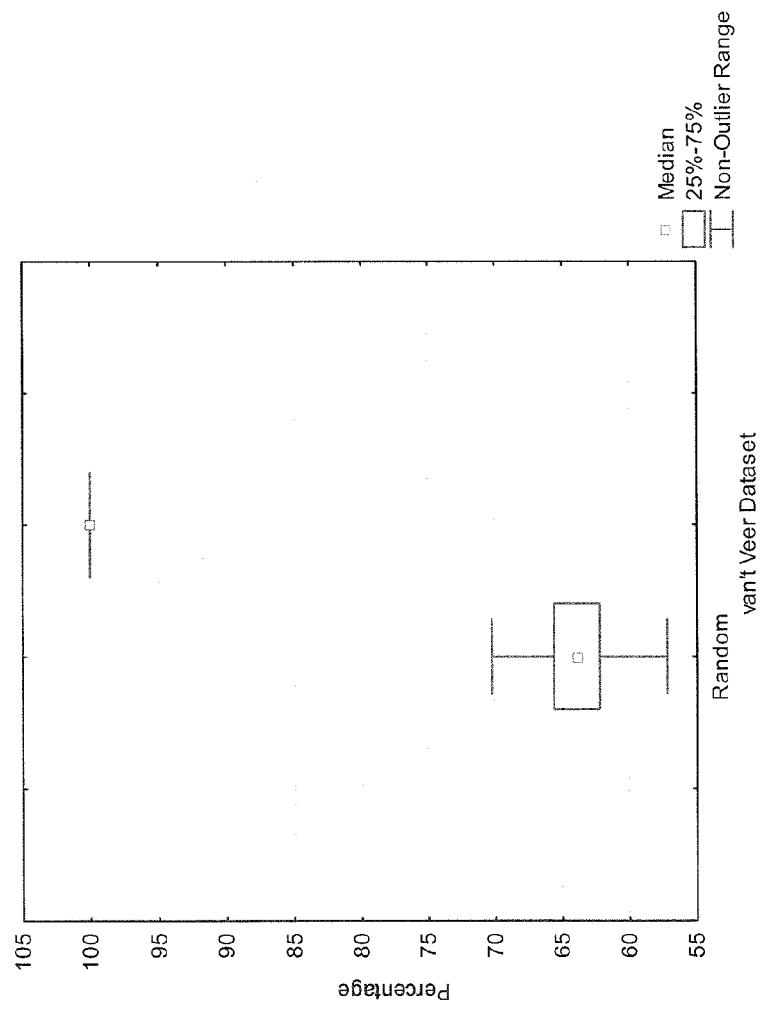

FIG. 18(a)-(c) highlights the significance between the performance of the randomly generated models and those developed with the stepwise approach for the van't Veer and West gene expression datasets (van't Veer, et al., 2002; West, et al., 2001).

These results show that a random classifier would indeed as expected lead to classification accuracies close to random, and therefore it can be said that the stepwise approach truly identifies subsets of inputs which predict well on unseen data.

Now it was necessary to investigate whether this stepwise approach would identify the same inputs if the analysis was run several different occasions, starting over each time with the same dataset. To achieve this, the stepwise analysis was run and trained on the van't Veer dataset with samples randomly split into training, test, and validation subsets 10, 20, 50 and 100 times and subsequently trained. This was then repeated five times to calculate how consistent the ranking of the individual inputs was with regards to model performance. This consistency was calculated for the top fifty most important inputs, and was the ratio of actual ranking based upon the average error of the model, to the average ranking over the multiple runs. These are summarised in Table 11.

TABLE 10

Summary results of random input selection

| Summary Statistic | Validation data accuracy | Validation data error |
| --- | --- | --- |
| Average | 64% | 0.495 |
| Standard Deviation | 0.024 | 0.014 |
| Standard Error | 0.0000245 | 0.0000141 |
| 95% confidence interval | 0.0000489 | 0.0000282 |
| Median | 64% | 0.495 |
| Inter Quartile Range | 62-66% | 0.485-0.504 |

TABLE 11

Summary of the consistency of inputs identified as importance using varying random sample cross validation data splits in step 1 of the analysis.

| Number of RSCV datasplits | Mean Group Consistency | 95% ci |
| --- | --- | --- |
| 10 | 0.547 | 0.009 |
| 20 | 0.708 | 0.009 |
| 50 | 0.859 | 0.010 |
| 100 | 0.880 | 0.013 |

There was a significant increase in consistency amongst the performance of inputs when increasing from 10 to 20 ($p=0.000$), and 20 to 50 RSCV datasplits ($p=0.000$), but not from 50 to 100 ($p=0.2213$). Interestingly, for all analyses, the same two inputs were ranked as first and second every time, with the majority of the variation in rankings appearing towards the bottom of the top 50 list, which accounts for the 14 and 12% variability in the 50 and 100 RSCV event models respectively. This showed step 1 to be extremely consistent in important input identification across multiple analyses.

The same procedure was then carried out for step 2, with the input identified as the most important across all the models in step 1 used to form the basis of this second step. Table 12 shows the average consistency ratios for step 2.

It is clear that consistency across multiple repeats of the analysis showed a dramatic decline, with only the 100 RSCV model retaining its consistency in input identification, and the improvement in consistent input performance was statistically significant ($p=0.000$) at each increment. The 50 and 100 RSCV models both identified the same input as number one ranked, and it therefore appears evident that a minimum of 50 RSCV datasplits is preferable to ensure that the same inputs are consistently identified as important multiple times in 80-90% of analyses.

TABLE 12

Summary of the consistency of inputs identified as importance using varying random sample cross validation data splits in step 2 of the analysis.

| Number of RSCV datasplits | Mean Group Consistency | 95% ci |
| --- | --- | --- |
| 10 | 0.140 | 0.004 |
| 20 | 0.487 | 0.011 |
| 50 | 0.657 | 0.009 |
| 100 | 0.811 | 0.009 |

CONCLUSIONS

The present example demonstrates one aspect of the novel stepwise ANN approaches of the invention as utilised in data mining of biomarker ions representative of disease status applied to different datasets. This ANN based stepwise approach to data mining offers the potential for identification of a defined subset of biomarkers with prognostic and diagnostic potential. These biomarkers are ordinal to each other within the data space and further markers may be identified by examination of the performance of models for biomarkers at each step of the development process. In order to assess the potential of this methodology in biomarker discovery, three datasets were analysed. These were all from different platforms which generate large amounts of data, namely mass spectrometry and gene expression microarray data.

The present technology is able to support clinical decision making in the medical arena, and to improve the care and management of patients on an individual basis (so called "personalised medicine"). It has also been shown that gene expression profiles can be used as a basis for determining the most significant genes capable of discriminating patients of different status in breast cancer. In agreement with van't Veer et al. (West, et al., 2001) it has been demonstrated that whilst single genes are capable of discriminating between different disease states, multiple genes in combination enhance the predictive power of these models. In addition to this, the results provide further evidence that ER+ and ER− tumours display gene expression patterns which are significantly different, and can even be discriminated between without the ER gene itself. This suggests that these phenotypes are not only explained by the ER gene, but a combination of other genes not necessarily primarily involved in the response of ER, but which may be interacting with, and modulating ER expression in some unknown fashion. Unlike some analysis methods, the present ANN stepwise approach takes each and every gene into account for analysis, and does not use various cut-off values to determine significant gene expression, which overcomes previous data analysis limitations. These models can then form a foundation for future studies using these genes to develop simpler prognostic tests, or as candidate therapeutic targets for the development of novel therapies, with a particular focus being the determination of the influence that these genes may have upon ER expression and development of lymph node metastasis. Given the relevance of the genes identified by this method and the applicability of these to a wider population this approach is a valid way of identifying subsets of gene markers associated with disease characteristics. Confidence in the identified genes is increased further still in that many of these genes have known associations with cancer.

To conclude, the present example demonstrates that by using novel ANN methodologies, it is possible to develop a powerful tool to identify subsets of biomarkers that predict disease status in a variety of analyses. The potential of this approach is apparent by the high predictive accuracies as a result of using the biomarker subsets identified. These biomarker subsets were then shown to be capable of high classification accuracies when used to predict for additional validation datasets, and were even capable of being applied to predict the ER and LN status of a dataset very different in origin from the one used in the identification of the important gene subsets. This in combination with the various validation exercises that have been conducted suggests that these biomarkers have biological relevance and their selection is not arbitrary or an artefact of the high dimensionality of the system as they were shown to be robust to cope with sampling variability and reproducible across different sample studies.

It will be understood that the embodiments described above are given by way of example only and are not intended to limit the invention, the scope of which is defined in the appended claims. It will also be understood that the embodiments described may be used individually or in combination.

The invention claimed is:

1. A method of determining a relationship between input data and one or more conditions comprising the steps of:
   receiving input data categorised into one or more predetermined classes of condition;
   training an artificial neural network with the input data, the artificial neural network comprising an input layer having one or more input nodes arranged to receive input data; a hidden layer comprising two or more hidden nodes, the nodes of the hidden layer being connected to the one or more nodes of the input layer by connections of adjustable weight; and, an output layer having an output node arranged to output data related to the one or more conditions, the output node being connected to the nodes of the hidden layer by connections of adjustable weight;
   determining relationships between the input data and the one or more conditions
   wherein the artificial neural network has a constrained architecture in which
   (i) the number of hidden nodes within the hidden layer is constrained; and,
   (ii) the initial weights of the connections between nodes are restricted and
   wherein the input data comprises data pairs, each data pair being categorised into the one or more conditions and comprising a parameter and associated parameter value, the training and determining steps comprising:
   (i) selecting a parameter within the input data, training the artificial neural network with corresponding parameter values and recording artificial neural network performance;
   (ii) repeating for each parameter within the input data;
   (iii) determining the best performing parameter in the input data;
   (iv) repeating steps (i) to (iii), each repetition adding one of the remaining parameters to the best performing combination of parameters, until artificial neural network performance is not improved.

2. A method of determining a relationship between input data and one or more conditions as claimed in claim 1, wherein the number of nodes in the hidden layer is in the range two to five.

3. A method of determining a relationship between input data and one or more conditions as claimed in claim 2, wherein there are two hidden nodes in the hidden layer.

4. A method of determining a relationship between input data and one or more conditions as claimed in claim 1, wherein the initial weights of connections between nodes have a standard deviation in the range 0.01 to 0.5.

5. A method of determining a relationship between input data and one or more conditions as claimed in claim 4, wherein the initial weights of connections between nodes have a standard deviation of 0.1.

6. A method of determining a relationship between input data and one or more conditions as claimed in claim 1, wherein the input data is grouped into a plurality of samples, each sample having an identical selection of data pairs.

7. A method of determining a relationship between input data and one or more conditions as claimed in claim 6, wherein the training step comprises:
   (i) selecting in a first selecting step the same parameter in each sample;
   (ii) training the artificial neural network with the parameter values associated with the selected parameter;
   (iii) recording the artificial neural network performance for the selected parameter;
   (iv) repeating the selecting and recording steps for each parameter in turn.

8. A method of determining a relationship between input data and one or more conditions as claimed claim 7, wherein the determining step further comprises:
   (i) ranking the performance of the artificial neural network for each selected parameter based on their recorded performance, and;
   (ii) selecting, in a second selecting step, the best performing parameter.

9. A method of determining a relationship between input data and one or more conditions as claimed in claim 8, wherein the training step further comprises:
   (i) selecting, in a further selecting step, a parameter from the remaining parameters in conjunction with the best performing parameter or parameters from the previous selecting step;
   (ii) training the artificial neural network with the parameter values associated with the selected parameters;
   (iii) recording, in a further recording step, the artificial neural network performance for the selected parameters, and;
   (iv) repeating the further selecting and recording steps for each of the remaining parameters in turn.

10. A method of determining a relationship between input data and one or more conditions as claimed in claim 9, wherein the training step further comprises repeating steps (i)-(iv) of claim 10 until no further substantial performance increase is gained.

11. A method of determining a relationship between input data and one or more conditions as claimed in claim 9, wherein, prior to the repeating step, the determining step comprises ranking the performance of the artificial neural network for each selected parameter arrangement based on their recorded performance and selecting the best performing parameters.

12. A method of determining a relationship between input data and one or more conditions as claimed in claim 9, wherein each time the number of input parameters is increased the number of input nodes is increased by one node.

13. A method of determining a relationship between input data and one or more conditions as claimed in claim 1, wherein the parameters represent genes and the parameter values represent gene expression data.

14. A method of determining a relationship between input data and one or more conditions as claimed in claim 1, wherein the parameters represent proteins and the parameter values represent activity function.

15. A method of determining a relationship between input data and one or more conditions as claimed in claim 1, wherein the artificial neural network is trained using random sample cross validation.

16. A method of determining a relationship between input data and one or more conditions as claimed in claim 15, wherein input data is randomly divided into three subsets, a first subset for training the network, a second subset to assess the network during the training process and a third subset to validate the trained network on unseen data.

* * * * *